(12) United States Patent
Leo et al.

(10) Patent No.: US 8,298,227 B2
(45) Date of Patent: Oct. 30, 2012

(54) TEMPERATURE COMPENSATED STRAIN SENSING CATHETER

(75) Inventors: Giovanni Leo, Chene Bougeries (CH); Nicolas Aeby, Geneve (CH); Yuri Vanenkov, Vernier (CH)

(73) Assignee: Endosense SA, Geneva (CH)

( * ) Notice: Subject to any disclaimer, the term of this patent is extended or adjusted under 35 U.S.C. 154(b) by 1102 days.

(21) Appl. No.: 12/152,473

(22) Filed: May 14, 2008

(65) Prior Publication Data

US 2009/0287092 A1 Nov. 19, 2009

(51) Int. Cl.
*A61B 19/00* (2006.01)

(52) U.S. Cl. .......................................... 606/41; 606/17

(58) Field of Classification Search ............... 606/27–34, 606/37–42, 45–50; 607/100, 102
See application file for complete search history.

(56) References Cited

U.S. PATENT DOCUMENTS

| | | |
|---|---|---|
| 4,757,194 A | 7/1988 | Simms |
| 4,873,989 A | 10/1989 | Einzig |
| 4,918,492 A | 4/1990 | Ferdinand et al. |
| 4,966,597 A | 10/1990 | Cosman |
| 4,983,034 A | 1/1991 | Spillman, Jr. |
| 5,014,709 A | 5/1991 | Bjelkhagen et al. |
| 5,018,529 A | 5/1991 | Tenerz et al. |
| 5,065,010 A | 11/1991 | Knute |
| 5,104,392 A | 4/1992 | Kittrell et al. |
| 5,122,137 A | 6/1992 | Lennox |
| 5,178,153 A | 1/1993 | Einzig |
| 5,201,317 A | 4/1993 | Kanazawa et al. |
| 5,202,939 A | 4/1993 | Belleville et al. |
| 5,279,793 A | 1/1994 | Glass |
| 5,289,256 A | 2/1994 | Gramling |
| 5,321,501 A | 6/1994 | Swanson et al. |
| 5,321,510 A | 6/1994 | Childers et al. |
| 5,348,019 A | 9/1994 | Sluss, Jr. et al. |
| 5,392,117 A | 2/1995 | Belleville et al. |
| 5,396,887 A | 3/1995 | Imran |
| 5,409,000 A | 4/1995 | Imran |
| 5,423,807 A | 6/1995 | Milder |
| 5,446,546 A | 8/1995 | Breidenbach et al. |

(Continued)

FOREIGN PATENT DOCUMENTS

DE  30 20 785  12/1981

(Continued)

OTHER PUBLICATIONS

U.S. Appl. No. 12/127,657, filed May 27, 2008, Leo.

(Continued)

*Primary Examiner* — Laura Bouchelle

(74) *Attorney, Agent, or Firm* — Patterson Thuente Christensen Pedersen, P.A.

(57) ABSTRACT

A strain sensing assembly implements thermal management and/or temperature measurement techniques to adequately mitigate against and compensate for temperature changes in optical fiber strain sensors of a distal end of a catheter. In one embodiment, the distal end of the catheter includes an end effector such as an ablation head that introduces significant thermal temperature changes proximate the distal end of the catheter. In one embodiment, a plurality of temperature sensors is utilized for accurate determination of each of a plurality of optical fiber strain sensors. In other embodiments, a single temperature sensor may be utilized by implementing thermal management techniques that adequately reduce temperature differences between the single temperature sensor and the plurality of optical fiber strain sensors.

25 Claims, 9 Drawing Sheets

U.S. PATENT DOCUMENTS

| | | |
|---|---|---|
| 5,575,787 A | 11/1996 | Abela et al. |
| 5,594,819 A | 1/1997 | Narendran et al. |
| 5,633,494 A | 5/1997 | Danisch |
| 5,645,065 A | 7/1997 | Shapiro |
| 5,662,108 A | 9/1997 | Budd et al. |
| 5,688,267 A | 11/1997 | Panescu et al. |
| 5,693,043 A | 12/1997 | Kittrell et al. |
| 5,696,863 A | 12/1997 | Kleinerman |
| 5,769,847 A | 6/1998 | Panescu et al. |
| 5,772,590 A | 6/1998 | Webster, Jr. |
| 5,782,828 A | 7/1998 | Chen et al. |
| 5,798,521 A | 8/1998 | Froggatt |
| 5,807,265 A | 9/1998 | Itoigawa et al. |
| 5,833,688 A | 11/1998 | Sieben et al. |
| 5,844,927 A | 12/1998 | Kringlebotn |
| 5,859,717 A | 1/1999 | Scobey et al. |
| 5,904,658 A | 5/1999 | Niederauer et al. |
| 5,906,614 A | 5/1999 | Stern et al. |
| 5,967,978 A | 10/1999 | Littmann et al. |
| 6,039,743 A * | 3/2000 | Quiachon et al. ............ 606/108 |
| 6,056,436 A | 5/2000 | Sirkis et al. |
| 6,063,078 A | 5/2000 | Wittkampf |
| 6,066,130 A | 5/2000 | Gregory et al. |
| 6,088,088 A | 7/2000 | Fortenberry |
| 6,102,926 A | 8/2000 | Tartaglia et al. |
| 6,113,590 A | 9/2000 | Fischer et al. |
| 6,113,593 A | 9/2000 | Tu et al. |
| 6,120,476 A | 9/2000 | Fung et al. |
| 6,120,520 A | 9/2000 | Saadat et al. |
| 6,129,667 A | 10/2000 | Dumoulin et al. |
| 6,133,593 A | 10/2000 | Boos et al. |
| 6,134,003 A | 10/2000 | Tearney et al. |
| 6,171,275 B1 | 1/2001 | Webster, Jr. |
| 6,173,091 B1 | 1/2001 | Reich |
| 6,175,669 B1 | 1/2001 | Colston et al. |
| 6,197,023 B1 | 3/2001 | Muntermann |
| 6,210,346 B1 | 4/2001 | Hall et al. |
| 6,217,574 B1 | 4/2001 | Webster |
| 6,226,542 B1 | 5/2001 | Reisfeld |
| 6,246,898 B1 | 6/2001 | Vesely et al. |
| 6,256,090 B1 | 7/2001 | Chen et al. |
| 6,262,822 B1 | 7/2001 | Obhi et al. |
| 6,266,542 B1 | 7/2001 | Stern et al. |
| 6,266,551 B1 | 7/2001 | Osadchy et al. |
| 6,272,371 B1 | 8/2001 | Shlomo |
| 6,276,215 B1 | 8/2001 | Berg |
| 6,310,990 B1 | 10/2001 | Putnam et al. |
| 6,324,918 B1 | 12/2001 | Gitis et al. |
| 6,370,412 B1 | 4/2002 | Armoundas et al. |
| 6,398,778 B1 | 6/2002 | Gu et al. |
| 6,425,894 B1 | 7/2002 | Brucker et al. |
| 6,451,009 B1 | 9/2002 | Dasilva et al. |
| 6,458,123 B1 | 10/2002 | Brucker et al. |
| 6,466,811 B1 | 10/2002 | Hassett |
| 6,470,205 B2 | 10/2002 | Bosselmann et al. |
| 6,470,286 B1 | 10/2002 | Seip et al. |
| 6,471,710 B1 | 10/2002 | Bucholtz |
| 6,546,271 B1 | 4/2003 | Reisfeld |
| 6,547,780 B1 | 4/2003 | Sinofsky |
| 6,558,378 B2 | 5/2003 | Sherman et al. |
| 6,563,970 B1 | 5/2003 | Bohnert et al. |
| 6,572,804 B2 | 6/2003 | Randall et al. |
| 6,602,242 B1 | 8/2003 | Fung et al. |
| 6,660,001 B2 | 12/2003 | Gregory |
| 6,674,928 B2 | 1/2004 | Johnson et al. |
| 6,695,808 B2 | 2/2004 | Tom |
| 6,701,931 B2 | 3/2004 | Sliwa, Jr. et al. |
| 6,852,109 B2 | 2/2005 | Winston et al. |
| 6,868,195 B2 | 3/2005 | Fujita |
| 6,898,338 B2 | 5/2005 | Kersey et al. |
| 6,915,048 B2 | 7/2005 | Kersey et al. |
| 6,947,637 B2 | 9/2005 | Smith |
| 6,955,675 B2 | 10/2005 | Jain |
| 6,986,769 B2 | 1/2006 | Nelson et al. |
| 7,050,662 B2 | 5/2006 | Behrmann et al. |
| 7,114,938 B2 | 10/2006 | Chou |
| 7,173,713 B2 | 2/2007 | Xu et al. |
| 7,241,986 B2 | 7/2007 | Wang |
| 7,460,964 B2 | 12/2008 | Mizota et al. |
| 7,466,879 B2 | 12/2008 | Tjin |
| 7,491,957 B2 | 2/2009 | Kitamura et al. |
| 8,048,063 B2 | 11/2011 | Aeby et al. |
| 2001/0021843 A1 | 9/2001 | Bosselmann et al. |
| 2002/0041722 A1 | 4/2002 | Johnson et al. |
| 2002/0041723 A1 | 4/2002 | Ronnekleiv et al. |
| 2002/0057859 A1 | 5/2002 | Walter et al. |
| 2002/0072680 A1 | 6/2002 | Schock et al. |
| 2004/0082844 A1 | 4/2004 | Vardi et al. |
| 2004/0165810 A1 | 8/2004 | Fujita |
| 2004/0206365 A1 | 10/2004 | Knowlton |
| 2004/0243119 A1 | 12/2004 | Lane et al. |
| 2005/0062979 A1 | 3/2005 | Zhu et al. |
| 2005/0213870 A1 | 9/2005 | Kersey et al. |
| 2006/0013523 A1 | 1/2006 | Childlers et al. |
| 2006/0045408 A1 | 3/2006 | Jones et al. |
| 2006/0100610 A1 | 5/2006 | Wallace et al. |
| 2006/0133715 A1 | 6/2006 | Belleville et al. |
| 2006/0200049 A1 | 9/2006 | Leo et al. |
| 2006/0263002 A1 | 11/2006 | Pocha et al. |
| 2007/0014490 A1 | 1/2007 | Silverbrook et al. |
| 2007/0041019 A1 | 2/2007 | Schmidt |
| 2007/0043338 A1 | 2/2007 | Moll et al. |
| 2007/0060847 A1 | 3/2007 | Leo et al. |
| 2007/0065077 A1 | 3/2007 | Childers et al. |
| 2007/0151390 A1 | 7/2007 | Blumenkranz et al. |
| 2007/0151391 A1 | 7/2007 | Larkin et al. |
| 2007/0156019 A1 | 7/2007 | Larkin et al. |
| 2007/0265503 A1 | 11/2007 | Schlesinger et al. |
| 2008/0009750 A1 | 1/2008 | Aeby et al. |
| 2008/0294144 A1 | 11/2008 | Leo et al. |
| 2009/0177095 A1 | 7/2009 | Aeby et al. |
| 2010/0063478 A1 | 3/2010 | Selkee |
| 2010/0087835 A1 | 4/2010 | Blumenkranz et al. |
| 2010/0094163 A1 | 4/2010 | Deladi et al. |
| 2011/0087112 A1 | 4/2011 | Leo et al. |
| 2012/0078138 A1 | 3/2012 | Leo et al. |

FOREIGN PATENT DOCUMENTS

| | | |
|---|---|---|
| DE | 38 28 550 | 3/1990 |
| EP | 0 281 405 | 9/1988 |
| EP | 0 934 728 | 8/1999 |
| EP | 1909650 | 4/2008 |
| EP | 2 047 797 | 4/2009 |
| JP | 09297078 | 11/1997 |
| JP | 10137200 | 5/1998 |
| JP | 2000227367 | 8/2000 |
| JP | 2004251779 | 9/2004 |
| WO | WO97/29678 | 8/1997 |
| WO | WO 97/32182 | 9/1997 |
| WO | WO 97/38637 | 10/1997 |
| WO | WO 98/19044 | 5/1998 |
| WO | WO 99/45994 | 9/1999 |
| WO | WO01/33165 | 5/2001 |
| WO | WO 01/33165 | 5/2001 |
| WO | WO 01/74252 | 10/2001 |
| WO | WO 02/19898 | 3/2002 |
| WO | WO 02/19903 | 3/2002 |
| WO | WO 02/23148 | 3/2002 |
| WO | WO 02/47751 | 6/2002 |
| WO | WO2004/002303 | 1/2004 |
| WO | WO 2005/059510 | 6/2005 |
| WO | WO 2006/092707 | 9/2006 |
| WO | WO2007/015139 | 2/2007 |
| WO | WO 2007/015139 | 2/2007 |
| WO | WO 2007015139 A2 * | 2/2007 |
| WO | WO 2007/050960 | 5/2007 |
| WO | WO 2007/111737 | 10/2007 |
| WO | WO 2008/000246 | 1/2008 |
| WO | WO 2008/003307 | 1/2008 |
| WO | WO 2008/045958 | 4/2008 |
| WO | WO 2009/114955 | 9/2009 |

OTHER PUBLICATIONS

U.S. Appl. No. 11/989,902, filed Feb. 1, 2008, Leo et al.
U.S. Appl. No. 12/127,657.
U.S. Appl. No. 11/989,902.

International Search Report (PCT/IB2009/051967), dated Mar. 16, 2010.
International Search Report (PCT/IB2008/002675), dated Dec. 2, 2009.
International Search Report (PCT/IB2010/0021), dated May 27, 2010.
Office Action of related application (U.S. Appl. No. 11/237,053), dated Apr. 12, 2010.
Office Action of related application (U.S. Appl. No. 11/753,429), dated Feb. 19, 2010.
FISO, "FOS-N Strain Sensor," FISO Technologies Inc., (2006), Canada.
Dickmann, "Experiment 03, Fabry Perot Resonator," (2003), pp. 1-19.
Precision Photonics Corporation, "Basic Physics and Design of Etalons," (2003), pp. 1-5.
Luna Innovations, "EFPI Techniques for Strain and Displacement Sensing," (Aug. 1999).
Luna Innovations, "Fiber Optic Bragg Grating Sensor," www.lunainnovations.com.products/shape.asp, (Aug. 2005).
Meller, "Extrinsic Fabry-Perot Interferometer System Using Wavelength Modulated Source," (Dec. 1996).
Uffelen, "Anchoring points for fibre optic strain sensors," Optical Techniques for Smart Structures and Structural Monitoring, (Feb. 1997), London, UK.
Lo, "Using in-fiber Bragg-grating sensors for measuring axial strain and temperature simultaneously on surfaces of structures," Optical Engineering, (Aug. 1998) vol. 37, Issue 8, pp. 2272-2276.
Dupont, "DuPont Zenite LCP liquid crystal polymer resin," Product and Property Guide, K-15415, May 2006.
Notification of the First Office Action for Chinese Application No. 20068007106.8 dated May 8, 2009.
Fernandez et al., "Multi-component force sensor based on multiplexed Fibre Bragg grating strain sensors" Measurement Science and Technology (2001) 810-813.
European Office Action for European Application No. 06795186.3 dated Nov. 25, 2010.
Yokoyama, MD, et al., "Novel Radiofrequency Ablation Catheter with Contact Force Sensor Predicts Lesion Size and Incidence of Steam Pop in Canine Model," Heart Rhythm Society, May 2007, Denver USA, vol. 4, Issue 5.
Shah et al., "Evaluation of a New Catheter Sensor for Real-Time Measurement of Tissue Contact," Heart Rhythm Society, May 2006, Boston, USA, vol. 3, Issue 5.
"The Unique Force Sensor Ablation Catheter," www.endosense.com/site/product.htm, Mar. 2007.
Application and File History for U.S. Appl. No. 11/237,053, filed Sep. 28, 2005, inventor Leo.
Office Action from U.S. Appl. No. 11/753,429 dated May 10, 2011.
Non-final Office Action dated Jun. 22, 2011 for U.S. Appl. No. 11/450,072.
European Office Action for European Application No. 06710474.5 dated Feb. 16, 2009.
European Office Action for European Application No. 06710474.5 dated Aug. 24, 2009.
Application and File History for U.S. Appl. No. 12/127,657, filed May 27, 2008, inventor Leo.
Application and File History for US Publication No. 2006/0200049 published Sep. 7, 2006, inventor Leo.
Application and File History for US Publication No. 2008/0009750 published Jan. 10, 2008, inventor Leo.
Application and File History for US Publication No. 2008/0294144 published Nov. 27, 2008, inventor Leo.
Application and File History for US Publication No. 2009/0177095 published Jul. 9, 2009, inventor Leo.
Application and File History for US Publication No. 2007/0060847 published Mar. 15, 2007, inventor Leo.
Application and File History for U.S. Appl. No. 11/989,902 filed Feb. 1, 2008, inventor Leo.
Paris-Seeley et al., "A compliance-independent pressure transducer for biomedical device-tissue interfaces," Biomed Instrum Technol. Nov.-Dec. 2000; 34(6): 423-31.
Brown, "Development of a Brillouin scattering based distributed fibre optic strain sensor," 2001.
Barrett, et al., "Extrinsic Fabry-Perot interferometer for measuring the stiffness of ciliary bundles on hair cells," Trans Biomed Eng. Mar. 1999; 46(3): 331-9.
Erdimer et al., "Fiberoptic measurement of tendon forces is influenced by skin movement artifact," J Biomech. Mar. 2003; 36(3): 449-55.
Schmidt et al., "Fiber-Optic Extrinsic Fabry-Perot Interferometer Strain Sensor with <50pm displacement resolution using three-wavelength digital phase demodulation," Optics Express, Apr. 9, 2001, vol. 8, No. 8.
"Fiber-optic strain-monitoring technology: BOTDR (Brillouin Optical Time-domain Reflectometer," NTT Innovative Technology Site.
Fearn et al., "An optical fiber transducer for single myofibril force measurement," Trans Biomed Eng. Nov. 1993; 40(11): 1127-32.
Komi et al., "Optic fibre as a transducer of tendomuscular forces," Eur J Appl Physiol 1996;72(3):278-80.
Del Villar et al., "Optimization of sensitivity in Long Period Fiber Gratings with overlay deposition," Optics Express, Jan. 10, 2005, vol. 13, No. 1.
Barb et al., "Versatile, high-speed force transducer using a laser fiode beam as an optical lever," J Appl Physiol 88: 308-314, 2000.
Rao, "Recent progress in applications of in-fibre Bragg grating sensors," Optics and Lasers in Engineering, vol. 31, Iss. 4, Apr. 1999, pp. 297-324.
Inaudi, "Application of optical fiber sensor in civil structural monitoring," The International Society for Optical Engineering, 2003.
Peirs et al., "Design of an Optical Force Sensor for Force Feedback during Minimally Invasive Robotic Surgery".
Zhang et al., "On SDM/WDM FFG Sensor Net for Shape Detection of Endoscope," Proceedings of the IEEE International Conference on Mechatronics & Automation, Jul. 2005.
Park et al, Force Sensing Robot Fingers using Embedded Fiber Bragg Grating Sensors and Shape Deposition Manufacturing.
Endosense receives CE mark for Tacticath force-sensing ablation catheter, May 4, 2009.
Endosense launches TOCCATA clinical study Oct. 7, 2008.
"Endosense achieves ISO 13485 certification" Aug. 12, 2008.
"Endosense unveils five groundbreaking abstracts on contact force measurement for catheter ablation" May 13, 2008.
Fuster et al., "ACC/AHA/ESC 2006 Guidelines for the Management of Patients with Atrial Fibrillation," Circulation Journal of the Americal Heart Association, 2006, Dallas, Texas, pp. e319-e321.
Calkins et al., "HRS/EHRA/ECAS Expert Consensus Statement on Catheter and Surgical Ablation of Atrial Fibrillation: Recommendations for Personnel, Policy, Procedures and Follow-Up," Eurospace (2007.
Natale et al., "Venice Chart Internatinoal Consensus Document on Atrial Fibrillation Ablation," Journal of Cardiovascular Electrophysiology, vol. 18. No. 5, May 2007.
Cappato et al., "Worldwide Survey on the Methods, Efficacy, and Safety of Catheter Ablation for Human Atrial Fibrillation," Journal of the Americal Heart Association, 2005.
Hasin et al., "Miniature Force Transducer for Myocardial Stimulation and Local Tension Measurements," IEEE Transactions on Biomedical Engineering, vol. BME-26, No. 2, Feb. 1979.
"Sensei X Robotic Catheter System for Electrophysiology Procedures," MedGadget, Sep. 18, 2009.
"Intellisense Fine Force Technology," Hansen Medical (website), http://www.hansenmedical.com/products/intellisense.aspx.
Hansen Medical product brochure, Sensie Robotic Catheter System.
Hansen Medical product brochure, Artisan extend Control Catheter.
Peirs et al., "A micro optical force sensor for force feedback during minimally invasive robotic surgery," Sensors and Actuators A 115 (2004) 447-455.
Xiao et al., "Fiber optic pressure sensor with self-compensation capability for harsh environment applications," Optical Engineering May, 2005, vol. 44(5).
European Office Action from European Application No. 06795186.3 dated Aug. 9, 2011.
European Office Action from European Application No. 11158967.7 dated Aug. 10, 2011.

Notice of Reasons for Rejection (translation) from Japanese Application No. 2007-557615 mailing date: Sep. 13, 2011.
International Preliminary Report on Patentability and Written Opinion from International Application No. PCT/IB2009/051967 date of issuance Nov. 17, 2010.
Application and File History for U.S. Appl. No. 11/237,053, filed Sep. 28, 2005, inventor Leo et al.
Application and File History for U.S. Appl. No. 11/450,072, filed Jun. 9, 2006, inventor Aeby.
Application and File History for U.S. Appl. No. 11/753,429, filed May 24, 2007, inventor Leo.
Application and File History for U.S. Appl. No. 12/352,426, filed Jan. 12, 2009, inventor Aeby.
Application and File History for U.S. Appl. No. 13/179,076, filed Jul. 8, 2011.
Application and File History for U.S. Appl. No. 13/096,647, filed Apr. 28, 2011, inventor Leo.
Application and File History for U.S. Appl. No. 11/436,926, filed May 15, 2006, inventor Leo.
Application and File History for U.S. Appl. No. 11/989,902, filed Feb. 1, 2008, inventor Leo.
European Office Action from European Application No. 09746251.9 dated Jan. 24, 2012.
Application and File History for U.S. Appl. No. 13/308,196, filed Nov. 30, 2011, inventors Leo et al.
Chinese Office Action from Chinese Application No. 200980125027.0 dated Jun. 29, 2012. English Translation of Chinese Office Action is provided.

* cited by examiner

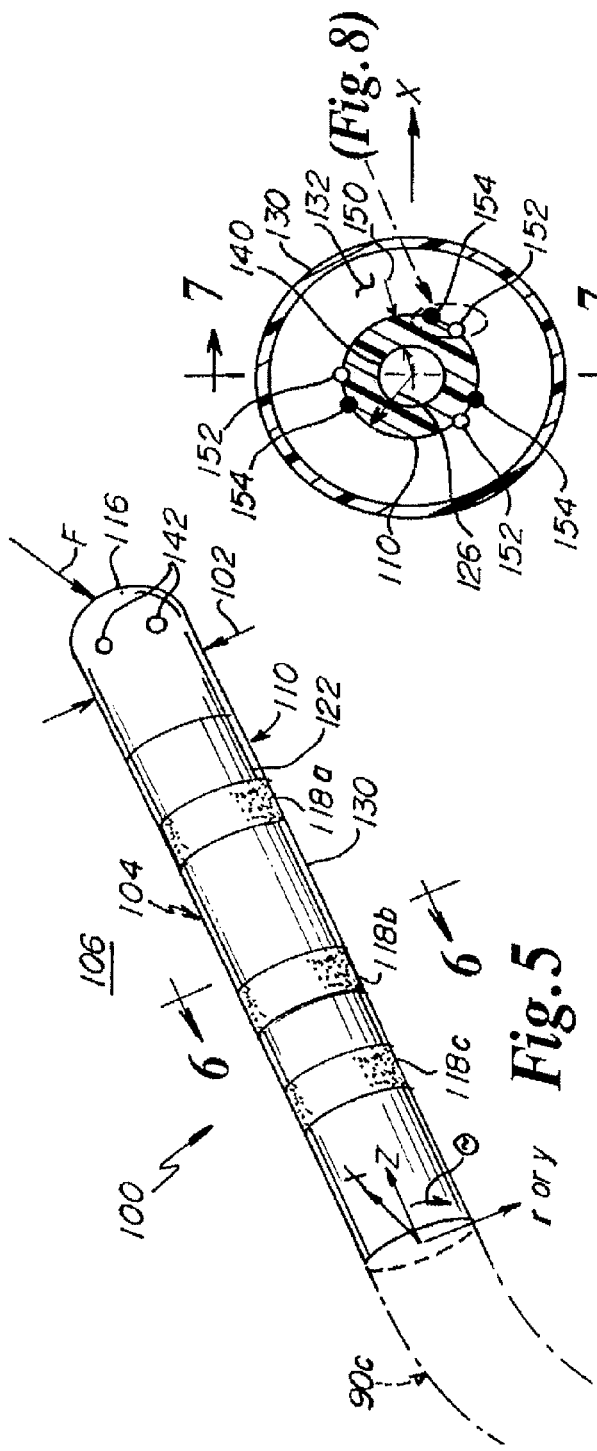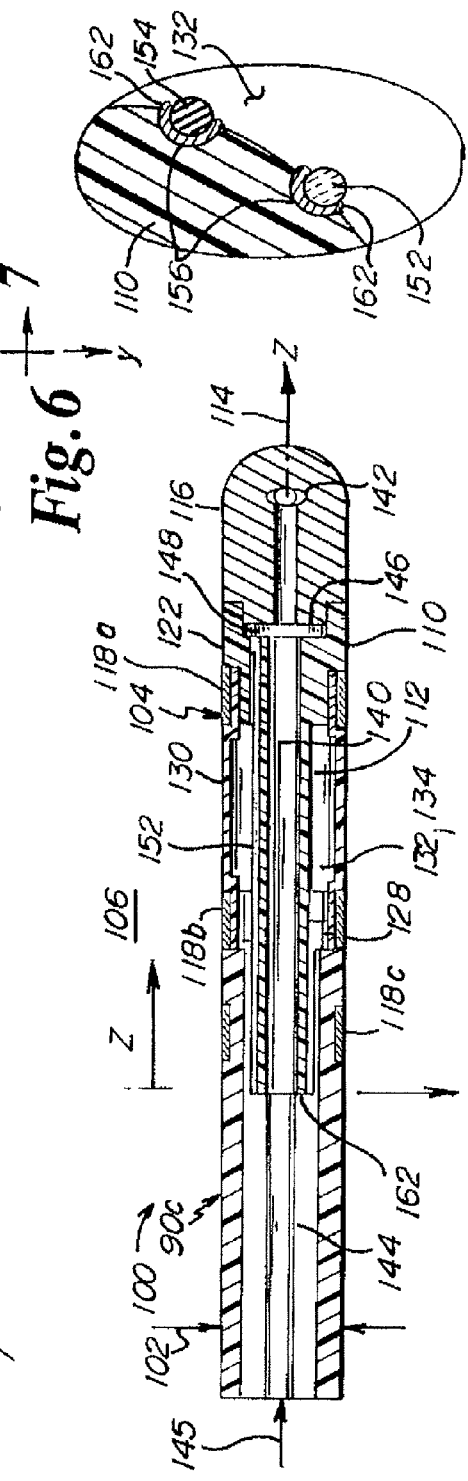

TEMPERATURE COMPENSATED STRAIN SENSING CATHETER

FIELD OF THE INVENTION

The present application is directed generally to surgical catheters with the ability to determine forces applied at a distal end of the catheter. More specifically, the present application is directed to a temperature compensated strain sensing catheter utilizing optical fiber strain sensors.

BACKGROUND OF THE INVENTION

Catheter systems utilizing light-based, optical fiber strain sensors to determine touching forces on a distal extremity of an end effector have found favor in recent years for the exploration and treatment of various organs or vessels with catheter-based diagnostic and treatment systems. Such light-based systems can be configured so that they are do not affect and are not affected by electromagnetic radiation environments.

One such light-based catheter system is described in U.S. Pat. No. 6,470,205 to Bosselman which describes a robotic system for performing surgery comprising a series of rigid links coupled by articulated joints. A plurality of Bragg gratings are disposed at the articulated joints so that the bend angle of each joint may be determined optically, for example, by measuring the change in the wavelength of light reflected by the Bragg gratings using an interferometer.

An article by J. Peirs et al., entitled "Design of an Optical Force Sensor for Force Feedback during Minimally Invasive Robotic Surgery," published by Katholieke Universiteit Leuven, Belgium, describes a tri-axial force sensor for use generating force feedback systems in a robotic surgery system. The apparatus includes a plurality of optical fibers that direct light onto a mirrored surface disposed adjacent to a distal tip of the device. The intensity of the light reflected from the mirrored surface is measured and may be correlated to the force required to impose a predetermined amount of flexure to the distal tip. The article describes a flexible and compact structure that may be used to produce variations in light intensity responsive to contact forces that deform the structure.

International Publication No. WO 2007/015139 to Leo, et al. (Leo), discloses a device and method for resolving a force vector (magnitude and direction) applied to the distal end of a catheter. Leo discloses the use of optical fiber strain elements in a catheter without increasing the profile of the catheter and is substantially immune to electromagnetic interference.

Generally, optical fiber strain sensors are sensitive to changes in temperature. For example, fiber Bragg grating (FBG) sensors include a fiber optic with uniformly spaced gratings formed or etched thereon. Light propagating through the fiber optic is reflected back by the gratings across a narrow wavelength bandpass. The bandpass of the reflected light is related to the spacing of the gratings in accordance with diffraction theory. The spacing is affected not only by the elastic strain experienced by the FBG, but also by thermal contraction and expansion of the FBG relative to a reference state. Temperature changes may also alter the refractive index of the FBG, further affecting wavelength bandpass that is reflected by the grating.

Another example of an optical fiber strain sensor that is generally sensitive to temperature is a Fabry-Perot strain sensor. Fabry-Perot strain sensors include a gap between the end of a transmitting fiber and a reflector. The transmitting fiber is often set up to be partially reflective. Light that enters the gap is inter-reflected between the reflector and the partially reflective transmitting fiber. The signal returned by a Fabry-Perot strain sensor is modulated in accordance with interference theory caused by the inter-reflections. The modulation is related to the dimension of the gap. The gap is affected not only by elastic strain of the structure that defines the gap, but also by thermal contraction and expansion of the structure relative to a reference state.

While optical fiber strain sensors can provide advantages for certain types of catheter procedures, the use of such strain sensors can be negatively impacted in situations involving temperature changes proximate the distal end of the catheter. What is needed is a device and method that adequately compensates for changes in the thermal state of strain sensing catheters utilizing optical fiber strain sensors.

SUMMARY OF THE INVENTION

Various embodiments of the invention include a strain sensing assembly that utilizes a polymer-based body and implements thermal management and/or temperature measurement techniques to adequately mitigate against and compensate for temperature changes in optical fiber strain sensors.

Thermal management techniques in accordance with various aspects of the invention may include reducing the axial conduction between a high temperature component of an end effector (e.g. an ablation head) and the optical fiber strain sensors. Thermal management technique in accordance with other aspects of the invention may include closer coupling of the optical fiber strain sensor to a controllable temperature sink, such as an irrigation flow stream. Still another thermal management technique in accordance with some embodiments of the invention may entail isolation of the optical fiber strain sensors from radial heating or cooling through the walls of the strain sensing assembly.

The temperature measurement techniques of the various embodiments may include measurement of a representative temperature of the optical fiber strain sensors. Such an approach may be adequate for applications or configurations where the thermal management of the optical fiber strain sensors produces a generally uniform temperature at a given axial location on the body of the strain sensing assembly. In other embodiments, the use of multiple temperature sensors may adequately characterize the thermal profile of the strain sensing assembly, providing representative temperatures of each optical fiber strain sensor.

Previous attempts have been made to compensate for changes in the temperature of optical fiber strain sensors. For example, U.S. Patent Application Publication No. 2007/0060847 to Leo et al. (Leo) and assigned to the assignee of the present application, describes a method for measuring a representative temperature of a plurality of optical fiber strain sensors and applying a correction that compensates for the effects of a change in temperature relative to a reference or calibration state. Leo also disclosed the use of a metallic flow conduit to which the optical fiber strain sensors were mounted for low thermal resistance between the optical fiber strain sensors and the irrigation flow stream.

However, a sensitivity problem was found to exist with the metallic flow conduit. A wall thickness of the metallic conduit designed to provide the necessary sensitivity to bending and compression forces was discovered to be too fragile for reliable operation. Increasing the wall thickness to a dimension that was mechanically reliable was found to impart too much stiffness and rendered the assembly inoperative due to loss of sensitivity.

One possible way to resolve the sensitivity/reliability conundrum is to utilize a material having less strength than metals so that the requisite sensitivity to bending and compression forces is realized with a thicker wall. Returning to polymer-based bodies, existing designs featured exterior walls at nearly full diameter with the fiber optic sensors mounted at or near the outer perimeter, while providing the requisite sensitivity to bending and axial compression forces.

However, in applying temperature correction to a polymer-based body having thicker walls, it was discovered that the representative temperature compensation technique was insufficient in certain circumstances. Polymers have substantially lower thermal conductivity than metals, which, coupled with thicker wall temperatures, reduces the thermal coupling between the optical fiber strain sensor and the irrigation flow. Thus, where the end effector generates and dissipates substantial thermal energy, such as in an ablation application, the temperature change of the strain sensing assembly is not always uniform, even at a given axial location. In such instances, the temperature rise of one optical fiber strain sensor may differ substantially from the temperature rise of another optical fiber strain sensor. Hence, the representative temperature may not accurately represent the temperature of all optical fiber strain sensors in the system.

By utilizing one or more of the various aspects of the present invention, the shortcomings of the prior art may be overcome.

Structurally, one embodiment of the invention includes a flexible elongate body adapted to be introduced into a patient during the medical procedure and including an end effector, the end effector including a strain sensing assembly, the strain sensing assembly including a deformable body, a plurality of optical fiber strain sensors operatively coupled with the deformable body, and a plurality of temperature sensors proximate the plurality of optical fiber strain sensors to determine the temperatures of the plurality of fiber strain sensors. In one embodiment, the deformable body is made of a liquid crystal polymer material. The plurality of temperature sensors may be of an equal or greater number than the plurality of optical fiber strain sensors. In one embodiment, each of the plurality of temperature sensors is positioned substantially closer to a corresponding one of the plurality of optical fiber strain sensors than to the other of the plurality of optical fiber strain sensors.

A sleeve may surround a portion of the deformable body, the plurality of optical fiber strain sensors and the plurality of temperature sensors being operatively coupled to the portion of the deformable body surrounded by the sleeve portion, the sleeve and the deformable body defining an annular gap therebetween. A thermal insulator comprising a solid insulation material may be disposed in the annular gap. The sleeve may include a structural member, such as a helical coil, that resists radial constriction from an external pressure increase without substantially restricting bending or axial compression of the deformable body. The optical fiber strain sensors may be, for example, fiber Bragg grating sensors or Fabry-Perot sensors. The temperature sensors may be thermocouples.

Certain embodiments may include an ablation head operatively coupled to a distal extremity of the deformable body, the ablation head having a base surface, the base surface being separated from the deformable body to define an axial gap therebetween. The deformable body may further include an irrigation passage that terminates at the axial gap for accommodation of an irrigation flow, the irrigation flow cooling the base surface of the ablation head.

In another embodiment, an end effector for a catheter is disclosed, comprising a deformable body, a plurality of optical fiber strain sensors operatively coupled to the deformable body, and a temperature sensor proximate the plurality of optical fiber strain sensors for determination of the temperature of the plurality of fiber strain sensors. A sleeve may surround a portion of the deformable body, with the plurality of optical fiber strain sensors and the temperature sensor being operatively coupled to the portion of the deformable body surrounded by the sleeve. In one embodiment, the sleeve and the deformable body define an annular gap therebetween. The sleeve may include a structural member that resists radial constriction from an external pressure increase without substantially restricting bending or axial compression of the deformable body. An insulator comprising a solid material may be disposed in the annular gap. The end effector may further include an ablation head operatively coupled to a distal extremity of the deformable body, the ablation head having a base surface, the base surface being separated from the deformable body to define an axial gap therebetween. The deformable body may include an irrigation passage that terminates at the axial gap for accommodation of an irrigation flow, the irrigation flow cooling the base surface of the ablation head.

In another embodiment of the invention, a strain sensing system is disclosed that includes a strain sensing assembly for an end effector of a catheter, the strain sensing assembly including a plurality of optical fiber strain sensors and a plurality of temperature sensors proximate the plurality of optical fiber strain sensors. An electromagnetic source may be operatively coupled with the plurality of optical fiber strain sensors for transmission of electromagnetic radiation to the plurality of optical fiber strain sensors. In this embodiment, at least one receiver operatively coupled with the plurality of optical fiber strain sensors for reception of a returned portion of the electromagnetic radiation, the returned portion being returned by the plurality of optical fiber strain sensors. Also, at least one signal conditioner operatively coupled with the plurality of temperature sensors for measurement of temperatures proximate the plurality of optical fiber strain sensors in this embodiment. A microprocessor may be operatively coupled with the receiver and the signal conditioner, as well as a digital storage device operatively coupled with the microprocessor, the digital storage device containing instructions for execution by the microprocessor.

The executable instructions may include determining a plurality of apparent strains, one for each of the plurality of optical fiber sensors, the plurality of apparent strains being inferred from the returned portion of electromagnetic radiation; determining a plurality of thermal bias components, one for each of the plurality of apparent strains, the plurality of thermal bias components being inferred from the temperatures proximate the plurality of optical fiber strain sensors; and inferring an elastic strain for each of the plurality of optical fiber sensors based on the apparent strain and the thermal bias component of each of the plurality of optical fiber sensors. A laser may be utilized as the electromagnetic source.

A method for determining a force exerted on a distal end of a catheter is also disclosed. Generally, a strain sensing assembly including a plurality of optical fiber strain sensors and a plurality of temperature sensors proximate the plurality of optical fiber strain sensors is provided. A plurality temperature measurements may be obtained, one each from the plurality of temperature sensors. A plurality optical fiber strain sensor temperatures may be inferred therefrom, one for each of the plurality of optical fiber strain sensors, the plurality of temperatures being inferred from the plurality of temperature measurements. A plurality of apparent strain measurements can also be obtained, one for each of the plurality of optical fiber strain sensors. A plurality of thermal bias components may be inferred, one each from the plurality of optical fiber strain sensors, the plurality of thermal bias components being inferred from the plurality of optical fiber strain sensor temperatures. A plurality of elastic strains may be inferred, one for each of the plurality of optical fiber strain sensors, from the plurality of apparent strain measurements and the plurality of thermal bias components. A magnitude and a direction of the force exerted on the distal end of the catheter may be inferred from the elastic strains. Inferring the plurality of thermal bias components may be performed implicitly or explicitly.

BRIEF DESCRIPTION OF THE DRAWINGS

FIG. 1A is a sectional view of the strain sensing assembly of FIG. 1;

FIG. 1B is a cutaway view of the strain sensing assembly of FIG. 1;

FIG. 5 is a perspective view of a temperature compensated strain sensing assembly in an embodiment of the invention;

FIGS. 6 and 7 are sectional views of the temperature compensated strain sensing assembly of FIG. 5;

FIG. 8 is an enlarged partial view of the sectional view of FIG. 6;

DETAILED DESCRIPTION

Figure 1:
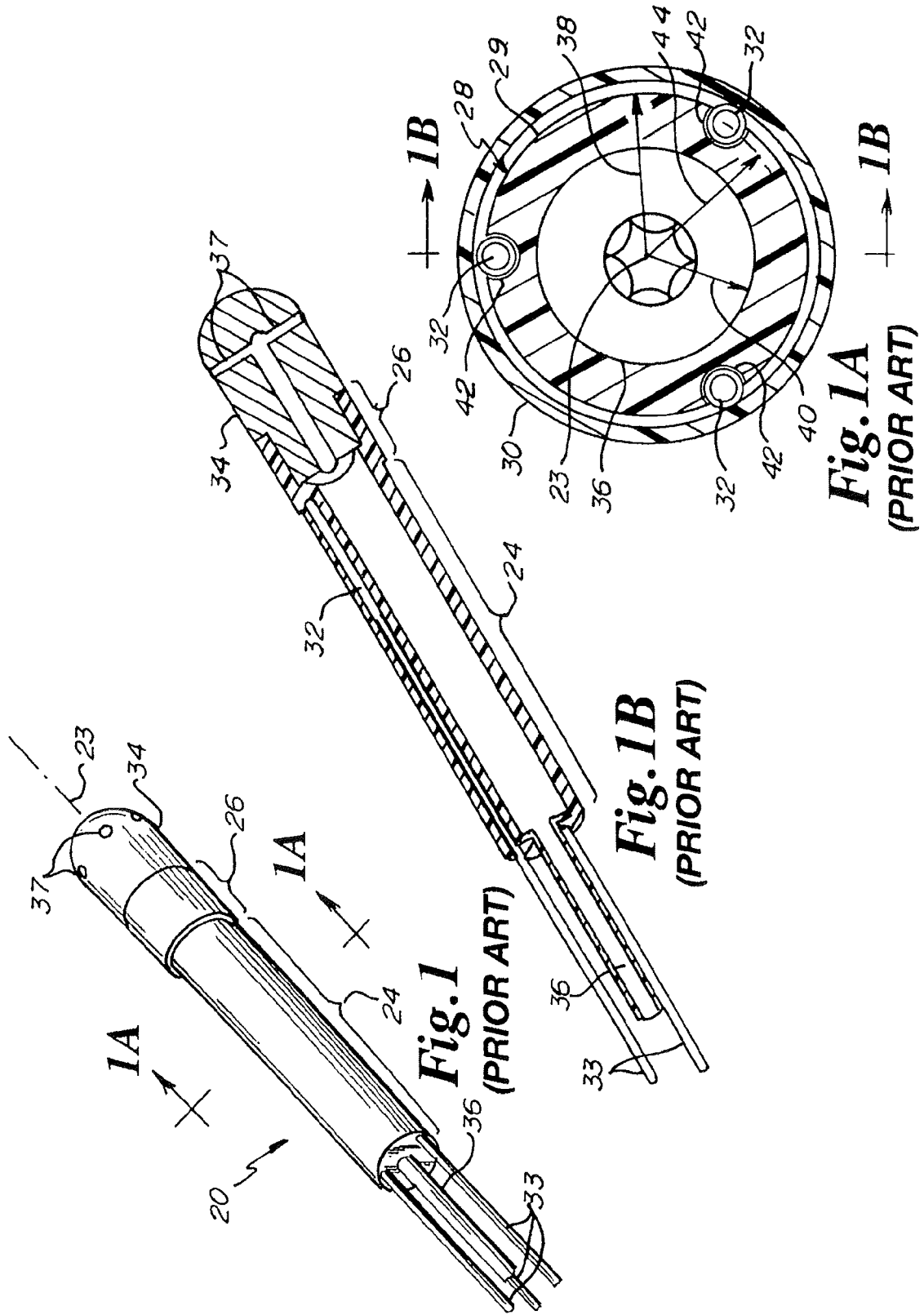
FIG. 1 is a perspective view of a strain sensing assembly operatively coupled to an ablation head.

Referring to FIGS. 1, 1A and 1B, a strain sensing assembly 20 comprising a deformable body 22 that defines a central axis 23 having a sensing portion 24 and a collar portion 26 is depicted. The sensing portion 24 of the strain sensing assembly 20 is further characterized as including a stem 28 having an outer surface 29 that is shrouded by a sleeve 30. A trio of fiber Bragg gratings 32, each sourced via a fiber optic 33, are operatively coupled to the stem 28. In the depicted embodiment, the collar portion 26 is operatively-coupled to an ablation head 34. An irrigation passage 36 passes through the stem 28 and ablation head 34, terminating at the exterior of the ablation head 34 via a plurality of transpiration passages 37.

In this embodiment, the strain sensing assembly 20 is characterized as having a stem radius 38 that is approximately 3½ times the radius 40 of irrigation passage 36. The fiber Bragg gratings 32 are mounted in a trio of grooves 42 on the outer surface 29 of the stem 28. The fiber Bragg gratings 32 are thereby located at a sensing radius 44 from the central axis 23 that is proximate the interior of the sleeve 30.

Figure 2:
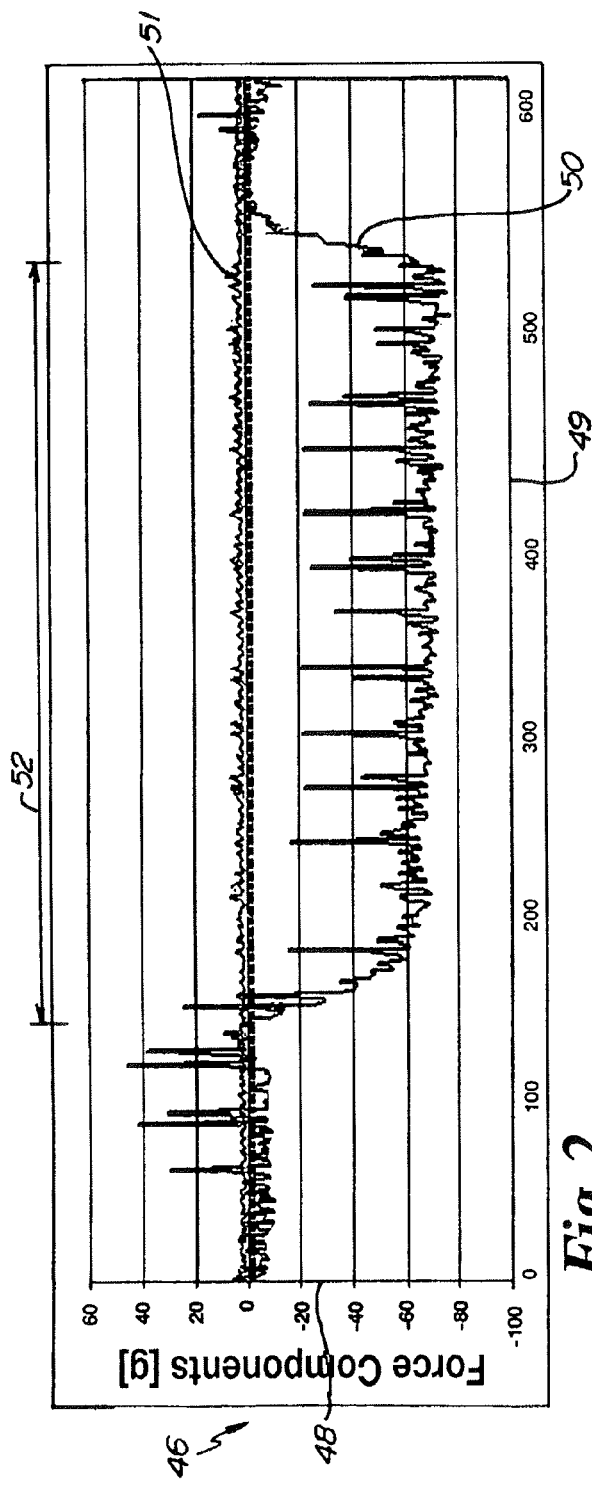
FIG. 2 is a graph of the bias of the resolved forces of an uncompensated strain sensing assembly during an ablation operation.

Referring to FIG. 2, a graph of representative uncorrected zero strain indications 46 produced by the strain sensing assembly 20 are depicted. The graph 46 presents a resolved force ordinate 48 in units of equivalent grams of force plotted against a time abscissa 49 in units of seconds. A resolved axial force 50 and a resolved transverse force 51 during a time frame surrounding an ablation operation 52 are presented on the graph 46. The ablation operation 52 was conducted with the ablation head 34 and the deformable body 22 having no contact with an external body; hence, the actual forces experienced by the strain sensing assembly 20 during the ablation operation 52 were zero.

The uncorrected zero force indications 46 illustrates a negative drift (i.e. an implied tension load) in the resolved axial force 50 indication during the ablation operation 52 while the resolved transverse force 51 remains substantially constant. The drift in the resolved axial force 50 is due to the effects of an increase in the temperature (e.g. the thermal expansion and a change in the refractive index) of the fiber Bragg gratings 32 during the ablation operation 52.

The substantial consistency of the resolved transverse force 51 of FIG. 2 indicates that all three of the fiber Bragg gratings 32 grew by an equal amount (i.e. the indicated force is nearly a pure tension force), suggesting that the heating of the fiber Bragg gratings 32 was substantially uniform. However, uniform heating of the fiber Bragg gratings 32 is not always realized.

Figure 3:
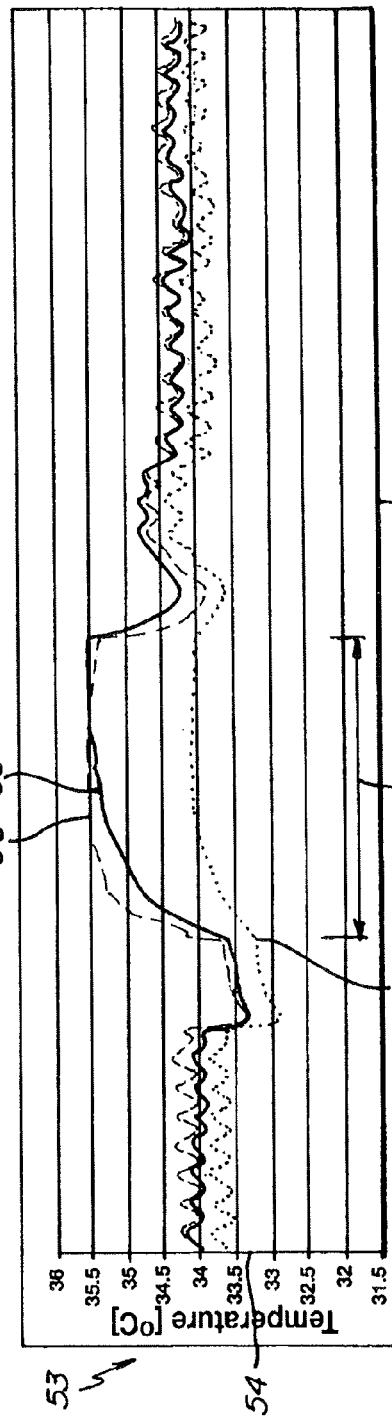
FIG. 3 is a graph of the output of temperature sensors on a strain sensing assembly body, the temperature sensors being at a common axial location and distributed at uniform intervals about the perimeter of the body of the strain sensing assembly.

Referring to FIG. 3, a time vs. temperature trace 53 is depicted for a strain sensing assembly/ablation head end effector that did not experience uniform heating. The time vs. temperature trace 53 presents a temperature ordinate 54 vs. a time abscissa 55, with traces of a first temperature trace 56, a second temperature trace 57 and a third temperature trace 58 during the timeframe surrounding and including an ablation interval 59.

The particular strain sensing assembly (not depicted) that generated the time vs. temperature trace 53 included three temperature sensors operatively coupled thereto that generated the three temperature traces 56, 57, 58, each of the temperature sensors being centered at the same axial position and spaced rotationally equidistant from each other (i.e. spaced 120° apart).

In this instance, the second temperature trace 57 indicates that a portion of the strain sensing assembly was about 1.5° C. cooler than the temperature traces 56 or 58 the time vs. temperature trace 53 demonstrates that the strain sensing assembly was not uniformly heated during the ablation interval 59. The error propagated by temperature uncertainties can be on the order of 10 grams/K for certain strain sensing assemblies. Accordingly, the temperature difference of the second temperature trace 57 may translate to an error on the order of 15 equivalent grams of the resolved forces.

The non-uniform heating of the strain sensing assembly may be caused by several factors, including the flow rate of the irrigation medium, the uniformity of the conduction path from a high temperature source such as an ablation head, and external influences that may cause uneven radial heat conduction. Therefore, for certain configurations of the strain sensing assembly, it has been discovered that one cannot rely on the assumption of a uniform heating of the optical fiber strain sensors.

Figure 4:
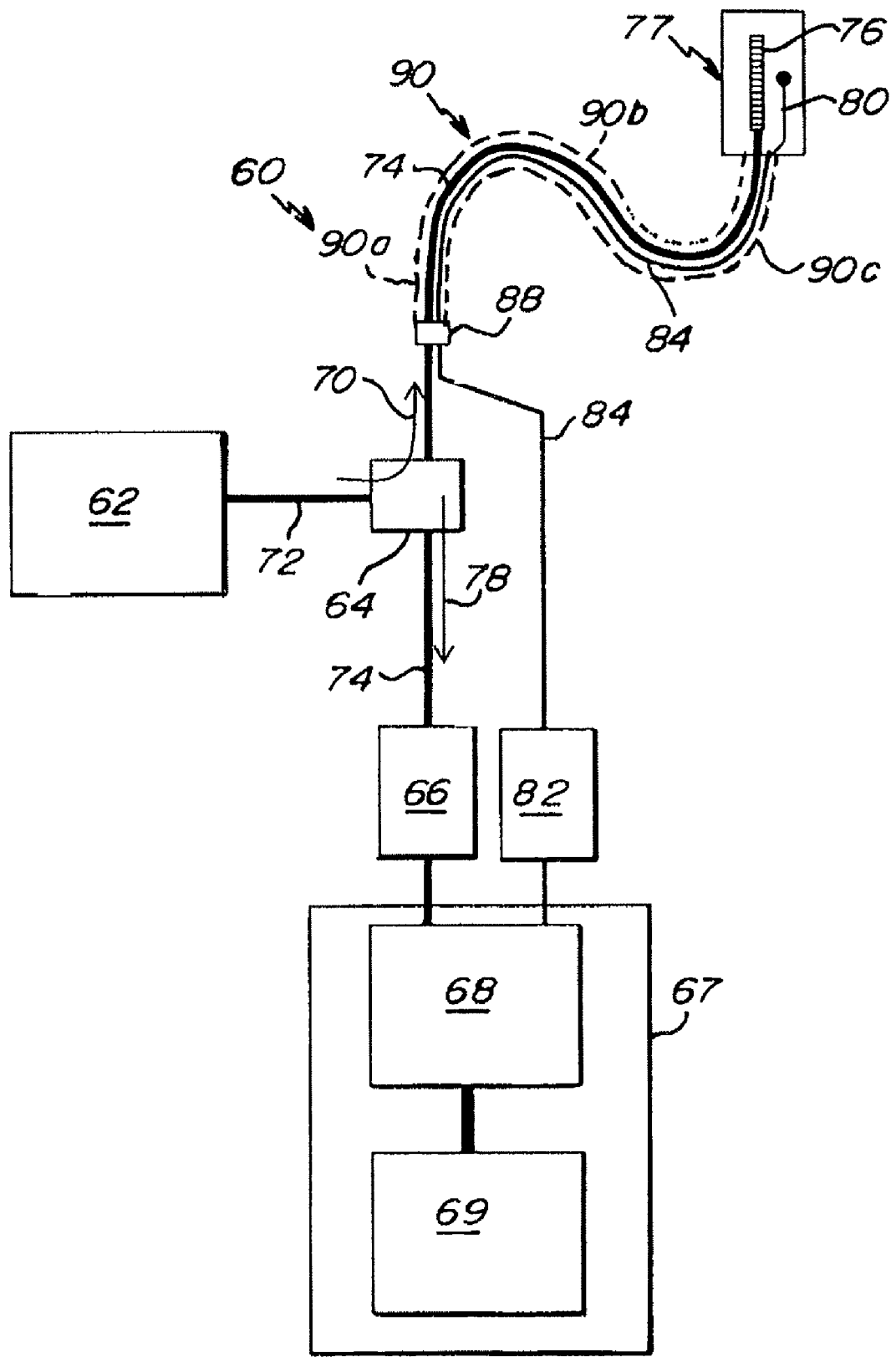
FIG. 4 is a temperature compensated strain sensing assembly in an embodiment of the invention.
Figure 10:
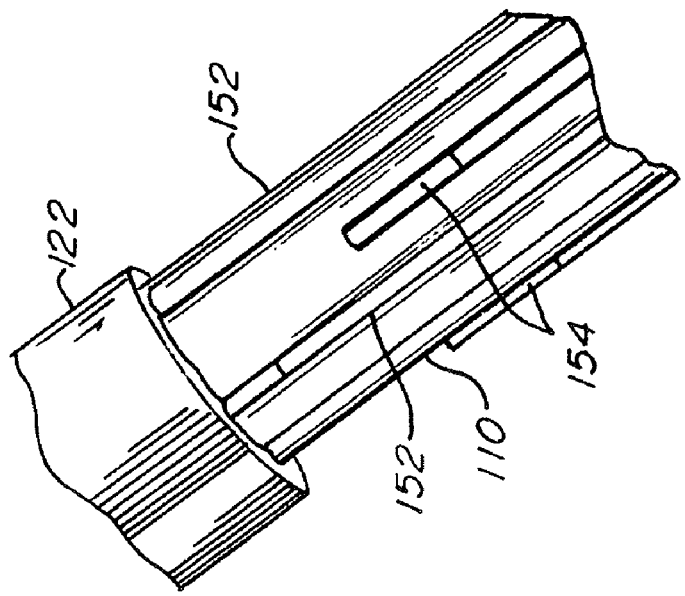
FIG. 10 is an enlarged view of the partial assembly of FIG. 9.

Referring to FIG. 4, an embodiment of a strain sensing system 60 is depicted in an embodiment of the invention. The strain sensing system 60 may comprise an electromagnetic source 62, a coupler 64, a receiver 66, an operator console 67 operatively coupled with a microprocessor 68 and a digital storage device 69. The electromagnetic source 62 may generate a transmitted component 70 of electromagnetic radiation, such as a laser or a broadband light source.

A transmission line 72 such as a fiber optic cable carries the transmitted component 70 to the coupler 64, which directs the transmitted radiation 70 through a transmitting/receiving line 74 to an optical fiber strain sensor 76. The transmitted component 70 may be transmitted to the optical fiber strain sensor 76 that is located within an end effector 77. A returned portion 78 of the transmitted radiation 70 that enters the optical fiber strain sensor 76 is returned back through the transmitting/receiving line 74 to the receiver 66.

The strain sensing system 60 may also comprise a temperature sensor 80 positioned proximate the optical fiber strain sensor 76 in the end effector 77. The temperature sensor 80 may be operatively coupled with a signal conditioner 82 via a signal cable 84. The signal conditioner 82 may be operatively coupled with the microprocessor 68.

The transmitting/receiving line 74 and the signal cable 84 may be coupled through a connector 88 as depicted in FIG. 4.

Though only one optical fiber strain sensor 76 is depicted, a plurality of optical fiber strain sensors and temperature sensors (not depicted) may be utilized, such as by parallel processing paths or by a multiplexing arrangement.

The transmitting/receiving line 74 may be operatively coupled with the optical fiber strain sensor 76 through a flexible, elongate catheter assembly 90. In one embodiment, the catheter assembly 90 comprises a proximal portion 90a, a middle portion 90b and a distal portion 90c. The distal portion 90c may include the end effector 77 containing the optical fiber strain sensor 76. The catheter assembly 90 may be of a hollow construction (i.e. having one or more lumens) or of a non-hollow construction (i.e. no lumen), depending on the application.

The strain sensing system 60 may interrogate the optical fiber strain sensor 76 at an exemplary and non-limiting rate in the range of 10-Hz to 1-kHz. The receiver 66 manipulates and/or converts the incoming returned portion 78 into digital signals for processing by the microprocessor 68. The receiver 66 may be chosen from a variety of receiving devices commercially available. For example, a receiver appropriate for Fabry-Perot optical fiber strain sensors is the FPI-HR signal conditioning module, produced by FISO Technologies of Quebec, QC Canada. A receiver appropriate for fiber Bragg grating strain sensors is the Model SM 125 Optical Sensing Interrogator, produced by Micron Optics of Atlanta, Ga. USA.

In one embodiment, the optical fiber strain sensor 76 is a fiber Bragg grating (FBG) and the returned portion 78 is a narrow wavelength band of radiation that is reflected from the gratings. The temperature sensor 80 may comprise any sensor of appropriate size and sensitivity in the temperature range of interest, such as a thermistor, resistance thermometer or thermocouple.

Referring to FIGS. 5 through 10, a temperature compensated strain sensing assembly 100 is depicted in an embodiment of the invention that may be utilized as the end effector 77 of FIG. 4. The temperature compensated strain sensing assembly 100 may have an overall diameter 102 and is depicted as being immersed in an operating environment 106. The temperature compensated strain sensing assembly 100 includes a deformable body 110 having an outer surface 112 and defining a central axis 114. In the depicted embodiment, the temperature compensated strain sensing assembly 100 comprises an ablation head 116 operatively coupled to the deformable body 110, and external sleeve electrodes 118a, 118b and 118c. An external force vector F is depicted as being applied to the ablation head 116. Dual coordinate systems (i.e. Cartesian x-y-z and cylindrical r-θ-z) are depicted at the base of the deformable body 110.

The deformable body 110 may include a collar portion 122, a neck portion 124 having a neck radius 126, a radial standoff structure 128, and an outer sleeve 130 that surrounds the neck portion 124. The outer sleeve 130 may bridge between the radial standoff structure 128 and the collar portion 122 and cooperate with the neck portion 124 to define an annular gap 132. The annular gap 132 may include a thermal insulator 134.

An irrigation passage 140 may be defined as passing through the deformable body 110 and the ablation head 116, and may terminate at irrigation outlets 142 formed in the ablation head 116. An irrigation tube 144 may be operatively coupled with the irrigation passage 140 for sourcing the irrigation passage 140 with irrigation fluid 145. An axial gap 146 may be defined between the deformable body 110 and a base surface 148 of the ablation head 116.

Note that relative to the strain sensing assembly 20 of FIG. 1A, the neck radius 126 is smaller and the irrigation passage 140 is of smaller diameter, defining a local wall thickness 150 of the deformable body 110. In this embodiment, a representative wall thickness 150 is approximately 200- to 300-micrometers; however, this wall thickness may not be representative or limiting for all embodiments.

A plurality of optical fiber strain sensors 152 may be operatively coupled to the deformable body 110. One or more temperature sensors 154 may also be operatively coupled to the deformable body 110. In one embodiment (depicted), the number of temperature sensors 154 is equal to the number of optical fiber strain sensors 152, one temperature sensor 154 for a corresponding optical fiber strain sensor 152, with the sensitive portion of temperature sensor 154 being mounted in close proximity to the corresponding optical fiber strain sensor 152. Channels 156 may be defined on the outer surface 112 of the deformable body 110 and the sensors 152, 152 coupled thereto. The sensitive portions of the optical fiber strain sensors 152 and temperature sensor(s) 154 may be substantially centered at the same axial location 160 relative to a proximal end 162 of the deformable body 110.

Figure 11:
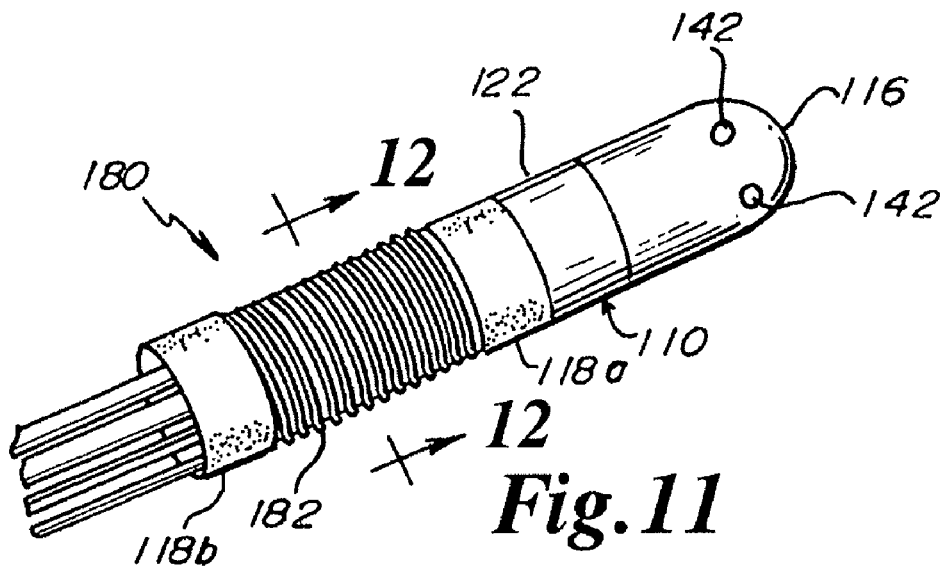
FIG. 11 is a perspective view of a partial assembly of a temperature compensated strain sensing assembly in an embodiment of the invention.
Figure 12:
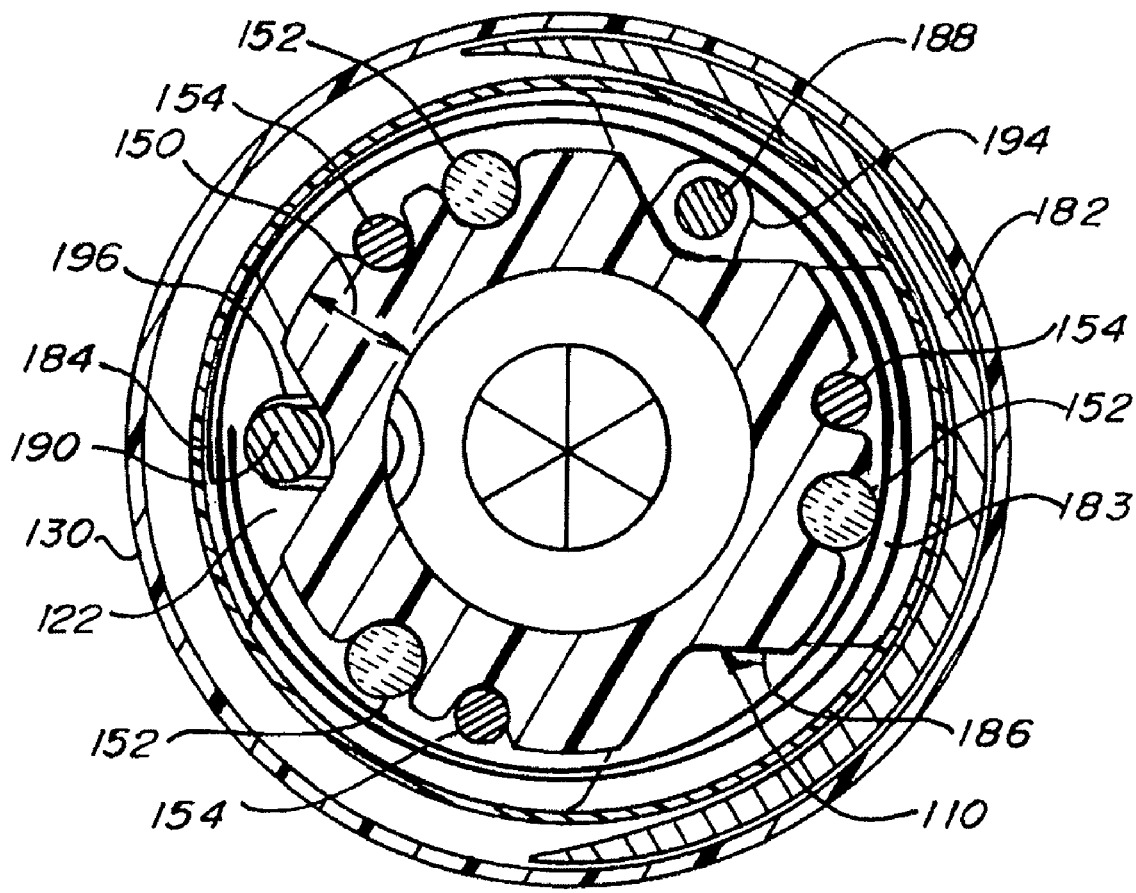
FIG. 12 is a sectional view of the partial assembly of FIG. 11.

Referring to FIGS. 11 and 12, a radially reinforced temperature compensated strain sensing assembly 180 is depicted in an embodiment of the invention. In the depicted embodiment, a helical coil 182 is arranged inside the outer sleeve 130. Alternatively, the helical coil 182 may be embedded within the outer sleeve 130. An annular gap 183 may be defined between the outer sleeve 130 or helical coil 182 and the deformable body 110. An insulation material 184 comprising a solid material may be disposed in the annular gap 183.

The outer sleeve 130 may be comprised of thermoplastic elastomer such as polyether block amide (marketed under the trade name PEBAX, a registered trademark of the Arkema France Corp. of Colombes, France). The insulation material 184 may comprise a polymide or MYLAR sheet material rolled around the deformable body 110 within the annular gap 183. (MYLAR is a registered trademark of Dupont Tejjin Films and is made from the resin Polyethylene Terephthalate (PET)).

Functionally, the helical coil 182 can provide radial stiffness while being compliant to axial and lateral forces applied on a distal portion of the end effector. Radial stiffness of the helical coil 182 can maintain the dimension of the annular gap 183 when the end effector experiences additional external pressure upon being inserted in a body or organ. By maintaining the dimension of the annular gap 183, the annular gap 183 and any insulative material that may be disposed therein substantially maintains its thermal insulative properties. Meanwhile, the compliance of the helical coil 182 to axial and bending forces enables the deformable body 118 to flex and compress without significant interference.

The depicted embodiment also includes V-grooves 186 formed in the deformable body 110 (FIG. 10) to accommodate passage of a power lead 188 and an ablation head temperature sensor 190. The power lead 188 and ablation head temperature sensor 190 may be routed through passageways 194 and 196, respectively in the collar portion 122 and operatively coupled to the ablation head 116. The passageways 194 and 196 may be filled with a suitable potting, for example, to prevent irrigation fluid 145 present in the axial gap 146 from entering the annular gap 183.

Generally, the deformable body 110 may comprise a polymeric material such as liquid crystal polymer (LCP) or polyetheretherketone (PEEK), such as disclosed in United States Patent Application Publication Nos. 2006/0200049 and 2007/0060847 to Leo et al., both of which are assigned to the assignee of the present application, and the disclosures of which are hereby incorporated by reference herein except for express definitions that may be included therein. The channels 156 may aid in the precise location of the sensitive portions of the sensors 152, 154. The optical fiber strain sensors 152 may comprise a fiber Bragg grating (FBG) sensor or a Fabry-Perot sensor.

Operative coupling of the optical fiber strain sensors 152 and/or the temperature sensor(s) 154 may be accomplished in one embodiment using a glue 162. The glue 162 may be placed in the channels 156 or on the optical fiber strain sensors 152 and the optical fiber strain sensors 152 place in the channels 156. Excess glue may be removed after placement. Some glues may enable placement of the optical fiber strain sensors 152 in the channels 156 followed by a coating or dabbing of glue on the optical fiber strain sensors 152 to secure it to the channels 156.

Another bonding technique may involve the use of a solvent designed to cause the material of the deformable body 110 to melt or flow while not affecting the material of the optical fiber strain sensors 152. The solvent may be applied to an area or zone of the deformable body 110 that encompasses at least a portion of the channels 156 where the optical fiber strain sensors 152 are to be mounted, and the optical fiber strain sensors 152 placed therein. Alternatively, the optical fiber strain sensors 152 may be temporarily held in place in the channels 156 of the deformable body 110 and the solvent applied as a coating over both. The flowing of the material in and around the channels 156 can cause a bond between the deformable body 110 and the optical fiber strain sensors 152. The solvent may be removed by a process such as washing or evaporation to arrest the melting process.

While the mounting and bonding techniques above are directed to an embodiment that includes channels 156, it is recognized that the same procedures may be utilized in the absence of channels 156.

Dimensionally, representative and non-limiting ranges for the various parameters include the overall diameter 102 of approximately 2.3-mm, the irrigation passage 140 of approximately 0.4- to 0.8-mm diameter, and the representative wall thickness 150 on the order of 200- to 300-micrometers.

Functionally, the reduced neck radius 126 of the neck portion 124 and/or the decreased diameter of the irrigation passage 140 relative to configurations such as depicted in FIG. 1 provides several advantages. For a given flow rate of irrigation fluid 145, the smaller diameter irrigation passage 140 increases the Reynolds number of the fluid flow, which can increase the convection heat transfer coefficient between the irrigation fluid 145 and the boundary of the irrigation passage 140, thereby enhancing the overall heat transfer between the irrigation fluid 145 and the optical fiber strain sensors 152. The reduced radius 126 may also provide a reduced cross-section of material, thereby reducing the thermal conductance through the neck portion 124 in the axial direction Z and the thermal coupling between the ablation head 116 and the optical fiber strain sensors 152. The wall thickness 150 of the neck portion 124 can also be tailored for a desired sensitivity (displacement) of the temperature compensated strain sensing assembly 100 in response to the force vector F. The reduced neck radius 126 of the neck portion 124 may also provide an increased thickness of the annular gap 132 relative to existing designs, thereby enhancing the thermal isolation between the operating environment 106 and the optical fiber strain sensors 152.

The channels 156, when present, may further decrease the thermal conduction path between the irrigation fluid 145 and the optical fiber strain sensors 154.

The axial gap 146, being flooded with irrigation fluid 145, may actively cool the base surface 148 of the ablation head 116 and mitigate against axial conduction of heat between the base surface 148 and the deformable body 110.

By these various thermal management aspects, various embodiments of the invention may cause the optical fiber strain sensors 152 to be dominated by the temperature of the irrigation fluid 145, with the influence of the ablation head 116 and the surroundings being secondary. An advantage of having the irrigation fluid 145 dominate the thermal state of the optical fiber strain sensors 152 is that the temperature of the irrigation fluid 145, as well as the convective coupling between the irrigation fluid 145 and the irrigation passage 140, tends to be more stable than the temperature of the ablation head 116 and the temperature and convective coupling between the operating environment 106 and the outer sleeve 130 during operation.

In operation, the temperature sensor(s) 154 may be utilized to compensate for the thermal expansion/contraction of the optical fiber strain sensors 152 relative to the calibration or nulling state. For configurations where the irrigation fluid 145 dominates the temperature of the neck portion 124, the temperature profile of the neck portion 124 may be substantially uniform or at least be substantially linear with respect to the axial coordinate Z, with no substantial variation tangentially in the temperature of the deformable body 110 at a given axial location (e.g. 160). In such conditions, a single temperature sensor 154 may be sufficient to accomplish the temperature compensation, particularly if the optical fiber strain sensors 152 and the temperature sensor 154 are positioned so the sensitive portions are centered about the same axial location 160.

Various configurations may produce non-uniform temperatures relative to the tangential coordinate $\theta$ at a given axial location Z (e.g. at axial location 160) during operation, as discussed above in reference to FIG. 3. Such condition may exist, for example, where structural and/or overall size requirements do not allow for a substantially reduced neck radius 126 relative to the overall diameter 102 of the temperature compensated strain sensing assembly 100. Non-uniform thermal profiles may also exist due in part to uneven or non-uniform thermal contact resistances between the ablation head 116 and the deformable body 110. In such circumstances, a plurality of the temperature sensors 154 may be preferable. The temperature sensors 154 may number the same as the optical fiber strain sensors 152, and each of the temperature sensors 154 may be located at a position that is closer to a corresponding one of the optical fiber strain sensors 152 than any of the other optical fiber strain sensors 152. In this way, the temperature of each of the optical fiber strain sensors 152 may be more closely approximated by the measurand produce by the corresponding temperature sensor 154.

In one embodiment, the optical fiber strain sensors 152 may comprise a fiber Bragg grating (FBG) section of length L and having gratings etched thereon. The FBG section may reflect a reference wavelength $\lambda r$ when the FBG section is at a reference temperature Tr at a reference time r when the reference (null) measurement is performed. In operation, the FBG section may reflect a wavelength $\lambda t$ at time t relative to the reference time r. The wavelength $\lambda t$ may differ from the reference wavelength $\lambda r$ due to a change in the length $\Delta L$ of the FBG section relative to the length L at time r. The change in the length $\Delta L$ may be caused by a strain on the FBG section, a temperature change that induces a thermal expansion of the FBG section, or a combination thereof. An apparent strain $\Delta L/L$ may therefore be expressed as $$\Delta L/L = C \cdot (\lambda t - \lambda r) = \epsilon + \alpha \cdot \Delta T \qquad \text{Eqn. (1)}$$

where $$\Delta T = Tt - Tr \qquad \text{Eqn. (2)}$$

and C is the coefficient of linearity between the FBG reflected wavelength and strain, $\epsilon$ is the elastic strain imposed on the FBG section, $\alpha$ is an equivalent coefficient of thermal expansion for the FBG section, and $\Delta T$ is the difference between the temperature Tt of the FBG section at time t and the reference temperature Tr. The apparent strain $\Delta L/L$ is so named because, without knowledge of the temperature and thermal behavior of the optical fiber sensor, the ratio $\Delta L/L$ would appear to be the result of an elastic strain.

Generally, it is desirable to mathematically isolate the elastic strain $\epsilon$ because it is primarily due to axial forces imposed on the FBG section. Isolating the elastic strain gives $$\epsilon = \Delta L/L - \alpha \cdot \Delta T = C \cdot (\lambda t - \lambda r) - \alpha \cdot \Delta T \qquad \text{Eqn. (3)}$$

For a plurality of FBG sections, Eqn. (3) may be expressed by $$\epsilon_i = (\Delta L/L)_i - \alpha_i \cdot \Delta T_i = C \cdot (\lambda t - \lambda r) - \alpha_i \Delta T_i \qquad \text{Eqn. (4)}$$

where the subscript i denotes one of a plurality of FBG sections.

But for the effects of temperature change on the optical fiber sensors, the apparent strain $\Delta L/L_i$ is equal to the elastic strains $\epsilon_i$. Accordingly, the product $\alpha_i \cdot \Delta_i$ may be considered a thermal bias component of the respective apparent strain $\Delta L/L_i$.

The equivalent coefficient of thermal expansion $\alpha$ is a parameter that is influenced by many factors. In some embodiments, $\alpha$ is influenced primarily by the coefficient of thermal expansion (CTE) of the deformable body 110. The CTE of the optical fiber strain sensor 152 may also be a contributing factor, as well as the CTE of the glue 162. The range of the CTEs of these components can vary substantially.

For example, the CTE of the optical fiber strain sensor can be on the order of about 0.3 micrometers per Kelvin ($\mu$/K), whereas the CTE of a deformable body constructed of LCP may have a CTE from 1- to 4-$\mu$/K. When utilized, the glue 162 can have a CTE on the order of 60$\mu$/K.

Furthermore, the refractive index of the optical fiber strain sensor 152 may be sensitive to changes in temperature. The sensitivity of the refractive index of some optical fibers is on the order of 10 picometers per Kelvin (pm/K). Depending on the configuration of the temperature compensated strain sensing assembly 100, 180 (e.g. geometry, CTEs of the various materials, sensitivity of the refractive index to temperature), the influence of the refractive index change may be dominant. For example, the resultant changes due to refractive index changes have been known to be an order of magnitude greater than the influence of CTE changes.

The true equivalent coefficient of thermal expansion $\alpha$ is generally affected by imperfections and/or non-repeatability of assembly. For example, the $\alpha$ of an optical fiber sensor may be substantially affected by minute differences in the amount of glue 162 utilized to affect the bond. Accordingly, each optical fiber strain sensor 152 in a given strain sensing assembly is generally characterized by its own unique equivalent coefficient of thermal expansion $\alpha$.

All of these thermal influences are rolled into the equivalent coefficient of thermal expansion $\alpha$. Moreover, the complexity of the parameter may cause cc to be non-linear. Accordingly, it is often preferable to determine the equivalent coefficient of thermal expansion $\alpha$ experimentally, such as by calibration, and for each optical fiber strain sensor in an assembly.

Equation (4) may be expressed in matrix form. Consider, for example, a temperature compensated strain sensing assembly 100 that implements three FBG sensors (i=1, 2, 3). The corresponding matrix expression is $$\begin{bmatrix} \varepsilon(1,t) \\ \varepsilon(2,t) \\ \varepsilon(3,t) \end{bmatrix} = \begin{bmatrix} 1 & 0 & 0 & -\alpha 1 & 0 & 0 \\ 0 & 1 & 0 & 0 & -\alpha 2 & 0 \\ 0 & 0 & 0 & 0 & 0 & -\alpha 3 \end{bmatrix} \cdot \begin{bmatrix} \Delta L/L(1,t) \\ \Delta L/L(2,t) \\ \Delta L/L(3,t) \\ \Delta T(1,t) \\ \Delta T(2,t) \\ \Delta T(3,t) \end{bmatrix} \qquad \text{Eqn. (5)}$$

or $$\begin{bmatrix} \varepsilon(1,t) \\ \varepsilon(2,t) \\ \varepsilon(3,t) \end{bmatrix} = \begin{bmatrix} C & 0 & 0 & -\alpha 1 & 0 & 0 \\ 0 & C & 0 & 0 & -\alpha 2 & 0 \\ 0 & 0 & C & 0 & 0 & -\alpha 3 \end{bmatrix} \cdot \qquad \text{Eqn. (6)}$$

$$\left( \begin{bmatrix} \lambda(1,t) \\ \lambda(2,t) \\ \lambda(3,t) \\ T(1,t) \\ T(2,t) \\ T(3,t) \end{bmatrix} - \begin{bmatrix} \lambda(1,r) \\ \lambda(2,r) \\ \lambda(3,r) \\ T(1,r) \\ T(2,r) \\ T(3,r) \end{bmatrix} \right)$$

where:

$\epsilon(i,t)$=elastic strain of the FBG section i at time t;

$\Delta L/L(i,t)$=apparent strain of FBG section i at time t;

$\Delta T(i,t)$=change in the temperature of the FBG section i at time t $\alpha i$=equivalent coefficient of thermal expansion of FBG section i $\lambda(i,r)$=wavelength reflected by FBG section i at time r (reference wavelength);

λ(i,t)=wavelength reflected by FBG section i at time t;

T(i,r)=temperature of FBG section i at time r (reference temperature); and

T(i,t)=temperature of FBG section i at time t.

When Eqns. (5) or (6) are executed, the products αi·ΔT(i,t) or αi·(T(i,t)−T(i,r)) are the inferred bias components for the FBG section i. The inferred bias components αi·ΔT(i,t) or αi·(T(i,t)−T(i,r)) may be determined implicitly as illustrated in Eqns. (5) and (6), or they may be determined explicitly for subtraction from the apparent strains ΔL/L(i,t).

As discussed above, some temperature compensated strain sensing assemblies may be configured to have negligible or otherwise tolerable radial temperature gradients between optical fiber sensors, such that a single temperature sensor is adequate for the temperature correction. The corresponding matrices for a single temperature measurement correction are as follows:

$$\begin{bmatrix} \varepsilon(1,t) \\ \varepsilon(2,t) \\ \varepsilon(3,t) \end{bmatrix} = \begin{bmatrix} 1 & 0 & 0 & -\alpha 1 \\ 0 & 1 & 0 & -\alpha 2 \\ 0 & 0 & 1 & -\alpha 3 \end{bmatrix} \cdot \begin{bmatrix} \Delta L/L(1,t) \\ \Delta L/L(2,t) \\ \Delta L/L(3,t) \\ \Delta T(t) \end{bmatrix} \quad \text{Eqn. (7)}$$

or $$\begin{bmatrix} \varepsilon(1,t) \\ \varepsilon(2,t) \\ \varepsilon(3,t) \end{bmatrix} = \begin{bmatrix} C & 0 & 0 & -\alpha 1 \\ 0 & C & 0 & -\alpha 2 \\ 0 & 0 & C & -\alpha 3 \end{bmatrix} \cdot \left( \begin{bmatrix} \lambda(1,t) \\ \lambda(2,t) \\ \lambda(3,t) \\ T(t) \end{bmatrix} - \begin{bmatrix} \lambda(1,r) \\ \lambda(2,r) \\ \lambda(3,r) \\ T(r) \end{bmatrix} \right) \quad \text{Eqn. (8)}$$

where T(r) and T(t) is the temperature of the FBG sections at time t and r, respectively, as determined by the single temperature sensor.

The elastic strains ε(i,t) are related to the forces experienced by the optical fiber strain sensors as a function of both the physical dimensions of, and the material properties of, the deformable body. Regardless of the number of temperature sensors utilized to obtain the temperature correction, the strain/force relationship may be expressed by $$\begin{bmatrix} \varepsilon(1,t) \\ \varepsilon(2,t) \\ \varepsilon(3,t) \end{bmatrix} = \begin{bmatrix} 1 & y1 & -x1 \\ 1 & y2 & -x2 \\ 1 & y3 & -x3 \end{bmatrix} \cdot \begin{bmatrix} \frac{1}{E_T \cdot A} & 0 & 0 \\ 0 & \frac{1}{E_F \cdot Ix} & 0 \\ 0 & 0 & \frac{1}{E_F \cdot Iy} \end{bmatrix} \cdot \begin{bmatrix} N(z,t) \\ M(x,t) \\ M(y,t) \end{bmatrix} \quad \text{Eqn. (9)}$$

where:
- xi and yi=coordinates of the FBG section i with respect to the center of gravity of the catheter cross-section;
- $E_T$=equivalent tension/compression Young modulus of the deformable body 110;
- $E_F$=equivalent flexural Young modulus of the deformable body 110;
- Ix=moment of inertia with respect to the x-axis;
- Iy=moment of inertia with respect to the y-axis;
- N(z,t)=normal force in direction of z-axis at time t;
- M(x,t)=bending moment with respect to x-axis at time t; and
- M(y,t)=bending moment with respect to y-axis at time t.

Equation (9) may be rearranged to solve for the normal force N(z,t) and the bending moments M(x,t) and M(y,t) as a function of the elastic strains ε(i,t):

$$\begin{bmatrix} N(z,t) \\ M(x,t) \\ M(y,t) \end{bmatrix} = \begin{bmatrix} E_T \cdot A & 0 & 0 \\ 0 & E_F \cdot Ix & 0 \\ 0 & 0 & E_F \cdot Iy \end{bmatrix} \cdot \begin{bmatrix} 1 & y1 & -x1 \\ 1 & y2 & -x2 \\ 1 & y3 & -x3 \end{bmatrix}^{-1} \cdot \begin{bmatrix} \varepsilon(1,t) \\ \varepsilon(2,t) \\ \varepsilon(2,t) \end{bmatrix} \quad \text{Eqn. (10)}$$

The components F(x,t), F(y,t) and F(z,t) of the external force vector F at time t may be resolved based on the positions of the FBG sections relative to the central axis 112 of the deformable body 110, assuming the deformable body 110 is substantially incompressible:

$$\begin{bmatrix} F(x,t) \\ F(y,t) \\ F(z,t) \end{bmatrix} = \begin{bmatrix} 0 & 0 & -\frac{1}{d} \\ 0 & \frac{1}{d} & 0 \\ -1 & 0 & 0 \end{bmatrix} \cdot \begin{bmatrix} N(z,t) \\ M(x,t) \\ M(y,t) \end{bmatrix} \quad \text{Eqn. (11)}$$

where d is the distance between the touching point of lateral forces and the cross-section with sensors (along z axis).

The solution of Eqns. (9) through (11) can provide a normal force F(norm, t) and a transverse force F(trans,t) applied to the external surface of the deformable body at time t, i.e., F(norm,t)=F(z,t) and F(trans,t)=(F(x,t)²+F(y,t)²)^(1/2). An angle of application $\gamma_t$ of the transverse force may be computed from Table I:

TABLE I

| $F_{x,t}$ | $F_{y,t}$ | $\gamma_t$ |
|---|---|---|
| ≥0 | ≥0 | arcsin(F(y, t)/F(trans, t)) |
| <0 | ≥0 | Π − arcsin(F(y, t)/F(trans, t) |
| <0 | <0 | Π + arcsin(F(y, t)/F(trans, t) |
| ≥0 | <0 | 2 * Π − arcsin(F(y, t)/F(trans, t) |

Equations (9) through (11) are related to the material properties of the deformable body or optical fiber strain sensors, such as the elastic moduli of the deformable body. Other values, such as the coordinate distances between the optical fiber strain sensors, the operative lengths of the interferometric gaps and the external surface of the deformable body may be subject to variations as a consequence manufacturing tolerances.

To improve the accuracy of the resolved direction and magnitude of the computed force vector, specific information for each deformable body may be stored in the digital storage device 69. Generally, the information make take the form of a data file that is input to console 67 prior to use of the temperature compensated strain sensing assembly 100. For example, the digital storage device 69 may comprise a memory chip associated with the transmitting/receiving line 74 in which such information is stored, or a bar code or a RFID tag located on the body of the strain sensor assembly 20 or on the packaging. Alternatively, data specific to an individual deformable body may be uploaded to console 67 from an item of removable storage (e.g., CD, ROM or nonvolatile RAM) or via secure download from the manufacturer's website.

The information specific to each deformable body may be obtained during a calibration step, conducted during manufacture of the deformable body, by subjecting the deformable body to a series of known force vectors. In this case, the foregoing equations may be collapsed so the normal and transverse forces may be computed directly from a strain-to-force conversion matrix:

$$F(t) = K(\epsilon(t) - \epsilon_o) \quad \text{Eqn. (12)}$$

where F(t) is the vector of forces [F(x,t), F(y,t), F(z,t)] (corresponding for example to the force vector F of FIG. 5), $\epsilon(t)$ is the vector of strains [$\epsilon_{1,t}, \epsilon_{2,t}, \epsilon_{3,t}$] measured by the individual optical fiber strain sensors 152, $\epsilon_o$ is the vector of strains [$\epsilon^o_1, \epsilon^o_2, \epsilon^o_3$] measured by the individual optical fiber strain sensors 152 with zero applied force, and K is a matrix computed when the deformable body is subjected to the series of known forces.

During the calibration step of manufacture, in constant temperature conditions, the deformable body may be subjected to the following forces in series: (1) a purely axial force of known magnitude F(z,t); (2) a lateral force of known magnitude F(x,t); and (3) a lateral force of known magnitude F(y,t) applied 90 degrees to the orientation of force F(x,t). When all of the forces [F(x,t), F(y,t), F(z,t)] and wavelengths are known, the force-to-strain conversion matrix K may be computed as:

$$K = F(\epsilon(t) - \epsilon_o)^{-1} \quad \text{Eqn. (13)}$$

or:

$$\begin{bmatrix} F_x & 0 & 0 \\ 0 & F_y & 0 \\ 0 & 0 & F_z \end{bmatrix} \begin{bmatrix} (\varepsilon_1 - \varepsilon_1^0) & (\varepsilon_1' - \varepsilon_1^0) & (\varepsilon_1'' - \varepsilon_1^0) \\ (\varepsilon_2 - \varepsilon_2^0) & (\varepsilon_2' - \varepsilon_2^0) & (\varepsilon_2'' - \varepsilon_2^0) \\ (\varepsilon_3 - \varepsilon_3^0) & (\varepsilon_3' - \varepsilon_3^0) & (\varepsilon_3'' - \varepsilon_3^0) \end{bmatrix}^{-1} = \begin{bmatrix} k_{11} & k_{12} & k_{13} \\ k_{21} & k_{22} & k_{23} \\ k_{31} & k_{32} & k_{33} \end{bmatrix} \quad \text{Eqn. (14)}$$

Force-to-strain conversion matrix K then may be stored in the digital storage device 69 associated with the corresponding deformable body, as disclosed herein. The values of the force-to-strain conversion matrix then may be input to console 67 when the deformable body is coupled to the console 67 using a bar code reader, input pad or direct electrical connection through transmitting/receiving line 74. Once matrix K is provided for a given deformable body, the normal force, transverse force and angle of application of the transverse force may be computed as described above and using Table I.

The values for the normal force, transverse force and angle of application of the transverse force, computed as described above, may be output as numerical values to a display monitor that forms part of console 67. In addition, a graphic including a variable size or colored arrow may be displayed pointing at a position on the circumference of a circle to visualize the magnitude and direction of the transverse force applied to the distal extremity of the deformable body. By monitoring this display, the operator may continuously obtain feedback concerning the contact forces applied to the distal extremity of the deformable body.

The invention may be practiced in other embodiments not disclosed herein, particularly where large local temperature gradients are generated in a surgical procedure. For example, various aspects of the disclosed embodiments may be utilized in a cryoablation context for the treatment of prostate cancer or other urinary maladies. Other aspects of the disclosed embodiments may find application in endoscopic applications, such as orthoscopic surgery or entry through open orifices such as the throat, nose or anus without departing from the spirit of the invention.

Figure 9:
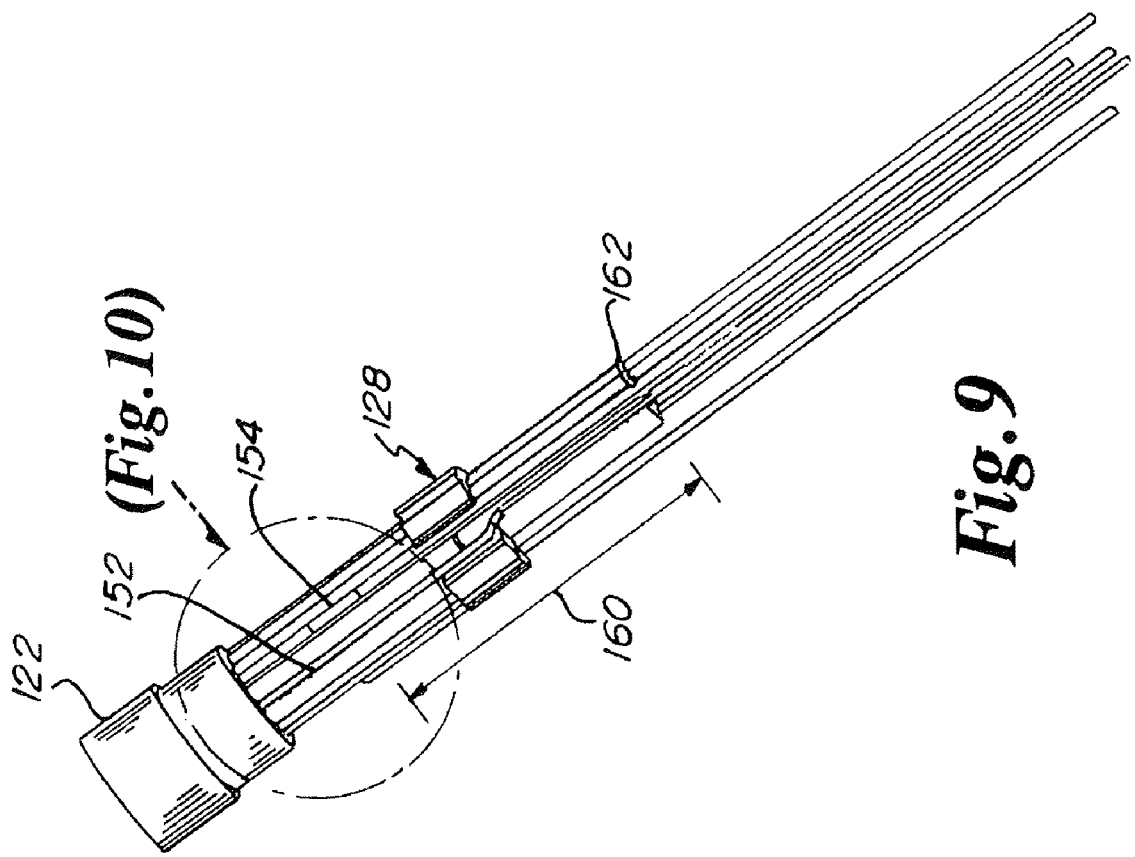
FIG. 9 is a perspective view of the temperature compensated strain sensing assembly of FIG. 5 in partial assembly.
Figure 13:
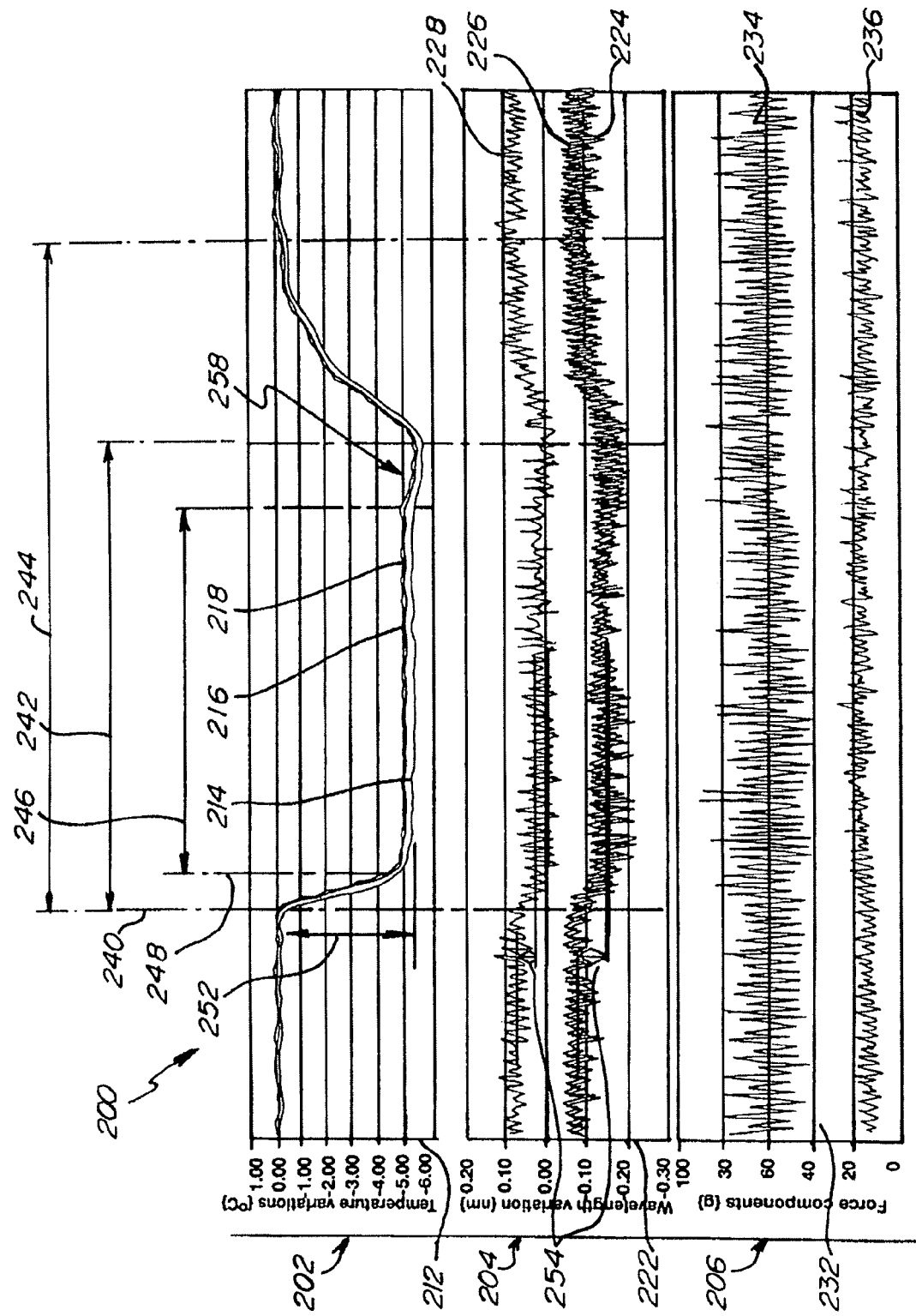
FIG. 13 is a multiple graph depicting temperature variation, wavelength variation and resolved forces of a temperature compensated strain sensing assembly using fiber Bragg gratings in an embodiment of the invention.

Referring to FIG. 13, an ablation analysis 200 is presented for the radially reinforced temperature compensated strain sensing assembly 180 in an embodiment of the invention. The optical fiber strain sensors 152 utilized for the ablation analysis 200 were FBG optical sensors. The temperature sensors 154 utilized were copper-constantan (type T) thermocouples. The optical fiber strain sensors 152 in the radially reinforced temperature compensated strain sensing assembly 180 were uniformly spaced in the tangential coordinate θ (i.e. spaced 120° apart). The temperature sensors 154 and the optical fiber strain sensors 152 were substantially centered at the same axial location on the deformable body 110, such as depicted in FIG. 9. Each of the temperature sensors 154 were located closer to a corresponding one of the optical fiber strain sensors 152 than to the other optical fiber strain sensors 154 (e.g. FIG. 12), and thus represented the temperature of the corresponding closest optical fiber strain sensor 154.

The ablation analysis 200 comprises a temperature variation graph 202, a wavelength variation graph 204 and a resolved force component graph 206, all obtained simultaneously with the radially reinforced temperature compensated strain sensing assembly 180 residing in a beating heart during an ablation operation. The three graphs 202, 204 and 206 share a common time abscissa 210 that spans about 80 seconds. The temperature variation graph 202 presents a temperature variation ordinate 212 in degrees Celsius for indication of the variation in indicated temperatures 214, 216 and 218 of the three temperature sensors 154. The wavelength variation graph 204 presents a wavelength variation ordinate 222 in nanometers for indication of central wavelength variation in the reflected signals 224, 226 and 228 from each of the trio of FBG optical sensors. The resolved force component graph 206 presents a force variation ordinate 232 for indication of the variation in a resolved axial force component 234 and a resolved transverse force component 236. The corrected reflected signals 224, 226, 228 and resolved forces 234, 236 were compensated according to the method described in Eqns. (1) through (6) and Eqns. (9) through (14).

The procedure followed for generating the ablation analysis 200 was to obtain null measurements for the various ordinates 212, 222 and 232 with the radially reinforced temperature compensated strain sensing assembly 180 at substantial thermal equilibrium with its surroundings and with an irrigation flow (e.g. irrigation flow 145 of FIG. 7) of 2 cubic centimeters per minute (ccm). The irrigation flow rate was increased to 17 ccm at an increased irrigation onset time 240 and maintained for an increased cooling time interval 242, after which the irrigation flow was returned to 2 ccm. The effect of the increased cooling time interval was to produce an interval of reduced temperature 244.

The ablation head 116 was energized continuously over an ablation operation time interval 246, starting at an ablation onset time 248. The temperature variation graph 202 indicates a temperature drop 252 during the increased cooling interval 242, caused by a dominant cooling effect of the increased flow rate in the irrigation fluid. Immediately after the ablation onset time 248, the indicated temperatures 214, 216 and 218 remains substantially stable for the duration of the ablation time interval 246. At the end of the increased cooling time interval 242 and the ablation time interval 248, the indicated temperatures 214, 216 and 218 returned to substantially the same level as the null measurement.

The wavelength variation graph 204 indicates a shift 254 in the time-averaged wavelength variations 222 of the reflected signals 224, 226, 228 during the interval of reduced temperature 244. The magnitude of the shift 254 is about 0.08-nm, which translates to an elastic force of about 80-gm for the particular strain sensing assembly under test.

Meanwhile the resolved forces 234, 236, which are compensated for temperature change, maintain essentially a steady time averaged level. That is, while these signals oscillate about respective mean values due to the pulsing nature of the application, the mean values themselves remain essentially steady, regardless of the changes in the indicated temperatures 214, 216 and 218 and reflected signals 224, 226, 228. Hence, the above disclosed apparatus and method effectively compensates for thermal induced changes in the optical fiber strain sensors 152.

After cessation of the ablation operation time interval 246, but before cessation of the increased cooling time interval 242, a temperature depression 258 is observed for the three indicated temperatures 214, 216, 218. The temperature depression 258 drops approximately 0.5° C. from the temperature levels established during the ablation operation time interval 246 to a substantially steady state level.

The temperature depression 258 is believed to be the result of reduced heat transfer, both radially and axially, through the radially enforced temperature compensated force sensor 180. Accordingly, the difference between the temperature during the ablation operation time interval 246 and the steady-state extremity of the temperature depression 258 for one of the indicated temperatures 214, 216, 218 illustrates the effect of the ablation operation. The small decrease of the temperature depression 258 relative to the temperature drop 252 implies that the temperature sensors 154 and the optical fiber strain sensors 152 are dominated by the flow of the irrigation fluid 145, and that the effects of ablation are secondary when the radially enforced temperature compensated force sensor 180 is being actively cooled by the irrigation fluid 145.

Figure 14:
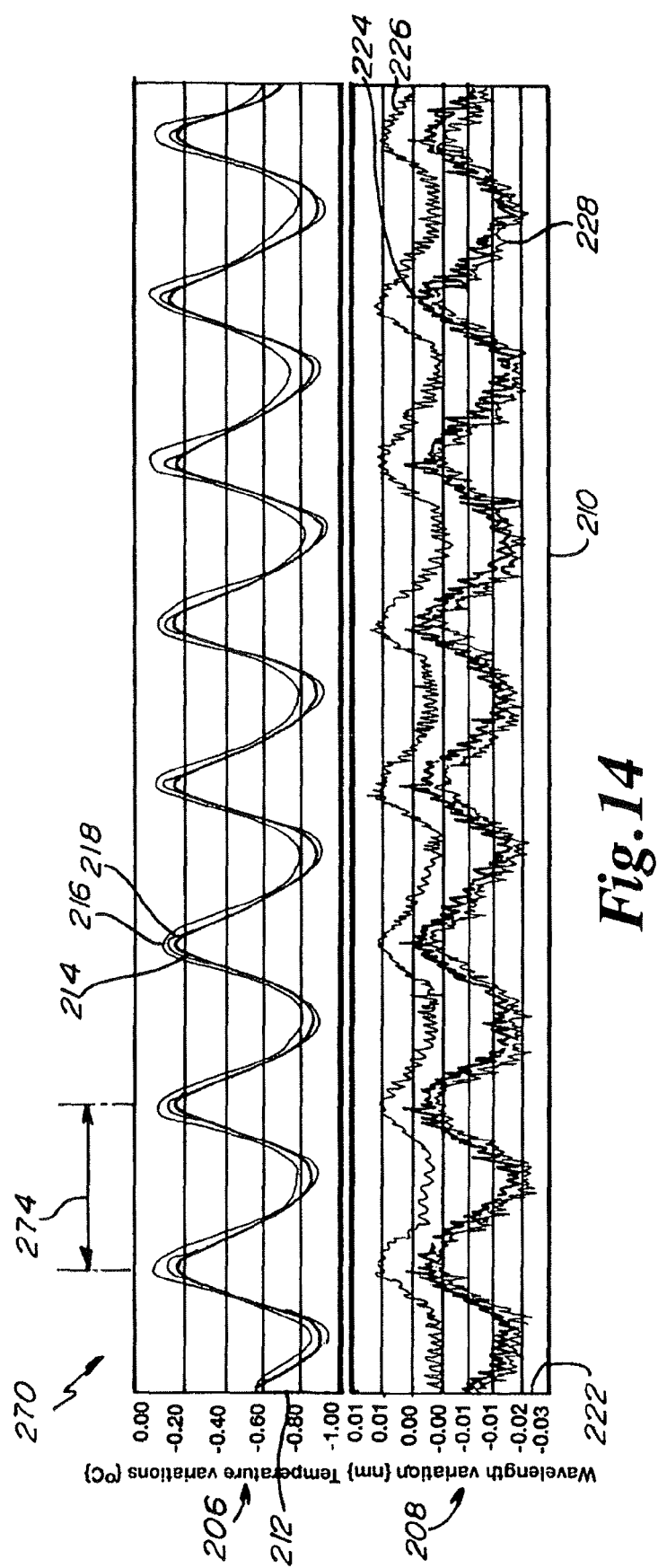
FIGS. 14 and 15 are multiple graphs depicting a calibration technique in an embodiment of the invention.
Figure 15:
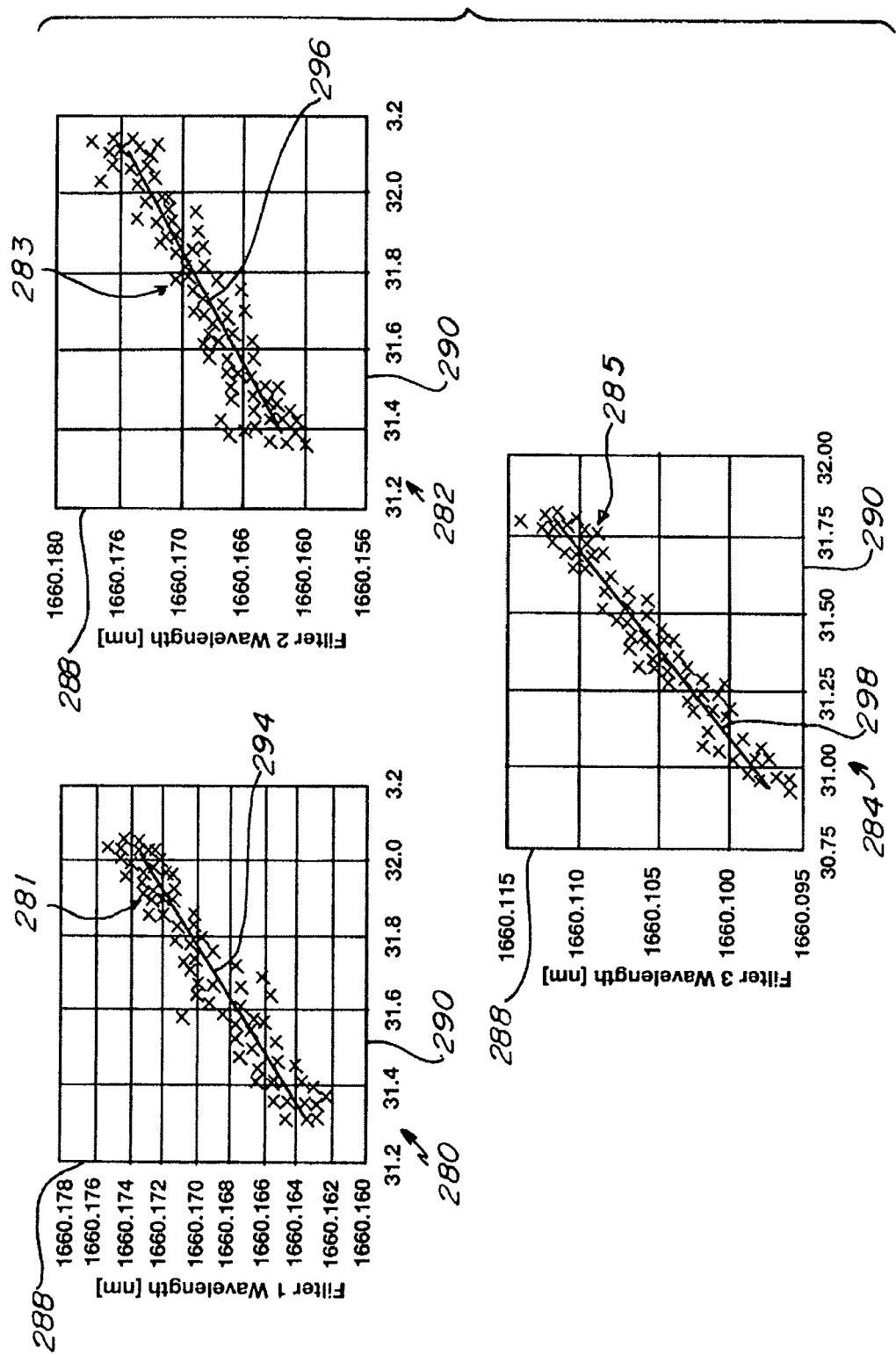

Referring to FIGS. 14 and 15, a method of calibrating or verifying the calibration of a temperature compensated strain sensing assembly of the present invention is described in an embodiment of the invention. FIG. 14 depicts a calibration data plot 270 of the temperature variation graph 206 and the wavelength variation graph 208, with the indicated temperatures 214, 216 and 218 are slowly oscillating with a time period 274 of approximately 6 seconds. The reflected signals 224, 226 and 228 also oscillate, closely tracking the indicated temperatures 214, 216 and 218. The amplitude of the temperature oscillation is just under 1° C.

FIG. 15 depicts a trio of correlation plots 280, 282 and 284. Each of the correlation plots 280, 282, 284 includes a reflected central wavelength ordinate 288 in nanometers and a temperature abscissa 290 in degrees Celsius. Each of the correlation plots 280, 282, 284 includes correlation data 281, 283 and 285 from one of the reflected signals 224, 226, 228 and a corresponding one of the indicated temperatures 214, 216, 218. That is, correlation plot 280 presents correlation data 281 of the wavelengths of the reflected signal 224 plotted against the indicated temperature 214, correlation plot 282 presents correlation data 283 of the wavelengths of the reflected signal 226 plotted against the indicated temperature 216, and correlation plot 284 presents correlation data 285 the wavelengths of the reflected signal 228 plotted against the indicated temperature 218.

Each of the correlation plots 280, 282 and 284 also presents a line fit 294, 296 and 298 of the respective temperature/ wavelength data. The line fit may be acquired using least-squares fitting techniques. The slope of the line fits 294, 296, 298 provides a calibration of the change in the central reflected wavelengths, which can then be utilized to provide the equivalent coefficients of thermal expansion $\alpha 1$, $\alpha 2$ and $\alpha 3$ of Eqn. (6).

The oscillating temperatures may be produced a variety of ways. For the calibration analyses of FIGS. 14 and 15, the oscillation was produced by immersing the radially reinforced temperature compensated strain sensing assembly 180 in a warm bath at a temperature of about 36° C. without the tip being in contact or otherwise experiencing an external force. Irrigation fluid at about 31° C. was then pumped through the strain sensing assembly 180 at a low flow rate (about 2 ccm) with a peristaltic pump. Peristaltic pumps produce an oscillatory flow which, if slow enough (long enough period) can cause an oscillatory cooling of the optical fiber strain sensors 152 of the strain sensing assembly 180. As the flow waxes and wanes through the strain sensing assembly 180, data for the calibration can be gathered and the correlations drawn.

The technique of this embodiment may be implemented as a stand alone calibration or as an in-situ calibration or calibration check. In a stand alone scenario, the difference between the hot and cold temperatures of the bath and irrigation fluid, respectively, may represent a large temperature range, so that the curve fit is over a temperature range representative of what is experienced in a high energy dissipation application such as ablation. The line fit in such a scenario may be utilized to account for non-linearities in the calibration, such as by fitting the data to a higher order polynomial. In an in-situ scenario, a line fit over a more narrow range of temperatures may be utilized. The data may be used to generate a calibration or to check the validity of a prior calibration.

References to relative terms such as upper and lower, front and back, left and right, or the like, are intended for convenience of description and are not contemplated to limit the invention, or its components, to any specific orientation. All dimensions depicted in the figures may vary with a potential design and the intended use of a specific embodiment of this invention without departing from the scope thereof.

Each of the additional figures and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "step for" are recited in the subject claim.

What is claimed is:

1. A catheter for use in a medical procedure, comprising:
a flexible elongate body adapted to be introduced into a patient during said medical procedure and including an end effector, said end effector including a strain sensing assembly, said strain sensing assembly including:
a deformable body;
a plurality of optical fiber strain sensors operatively coupled with said deformable body; and
a plurality of temperature sensors proximate said plurality of optical fiber strainsensors to determine the temperatures of said plurality of fiber strain sensors,
wherein a first of said plurality of temperature sensors is positioned substantially closer to a first of said optical fiber strain sensors than to the other of said plurality of optical fiber strain sensors, and wherein a second of said plurality of temperature sensors is positioned substantially closer to a second of said optical fiber strain sensors than to the other of said plurality of optical fiber strain sensors.

2. The catheter of claim 1 wherein said plurality of temperature sensors are of an equal or greater number than said plurality of optical fiber strain sensors.

3. The catheter of claim 1 further comprising a sleeve that surrounds a portion of said deformable body, said plurality of optical fiber strain sensors and said plurality of temperature sensors being operatively coupled to said portion of said deformable body, said sleeve and said deformable body defining an annular gap therebetween.

4. The catheter of claim 3 further comprising a solid insulation material disposed in said annular gap.

5. The catheter of claim 3 wherein said sleeve includes a structural member that resists radial constriction from an external pressure increase without substantially restricting bending or axial compression of said deformable body.

6. The catheter of claim 5 wherein said structural member comprises a helical coil.

7. The catheter of claim 1, wherein said optical fiber strain sensors are fiber Bragg grating sensors.

8. The catheter of claim 1, wherein said temperature sensors are thermocouples.

9. The catheter of claim 1, wherein said deformable body comprises a liquid crystal polymer material.

10. The catheter of claim 1 further comprising:
an ablation head operatively coupled to a distal extremity of said deformable body, said ablation head having a base surface, said base surface being separated from said deformable body to define an axial gap therebetween,
wherein said deformable body includes an irrigation passage that terminates at said axial gap for accommodation of an irrigation flow, said irrigation flow cooling said base surface of said ablation head.

11. An end effector for a catheter, comprising:
a deformable body;
a plurality of optical fiber strain sensors operatively coupled to said deformable body;
a temperature sensor proximate said plurality of optical fiber strain sensors for determination of the temperature of said plurality of fiber strain sensors;
a sleeve that surrounds a portion of said deformable body, said plurality of optical fiber strain sensors and said temperature sensor being operatively coupled to said portion of said deformable body surrounded by said sleeve, said sleeve and said deformable body defining an annular gap therebetween, said sleeve including a structural member that resists radial constriction from an external pressure increase without substantially restricting bending or axial compression of said deformable body; and
a thermal insulator comprising a solid material disposed in said annular gap.

12. The end effector of claim 11 further comprising:
an ablation head operatively coupled to a distal extremity of said deformable body, said ablation head having a base surface, said base surface being separated from said deformable body to define an axial gap therebetween,
wherein said deformable body includes an irrigation passage that terminates at said axial gap for accommodation of an irrigation flow, said irrigation flow cooling said base surface of said ablation head.

13. The end effector of claim 11, wherein said solid material comprises a rolled sheet material.

14. The end effector of claim 13, wherein said rolled sheet material comprises one of a polymide and a polyethylene terephthalate material.

15. The end effector of claim 11, wherein said structural member comprises a helical coil.

16. A strain sensing system, comprising:
a strain sensing assembly for an end effector of a catheter, said strain sensing assembly including a plurality of optical fiber strain sensors and a plurality of temperature sensors proximate said plurality of optical fiber strain sensors;
an electromagnetic source operatively coupled with said plurality of optical fiber strain sensors for transmission of electromagnetic radiation to said plurality of optical fiber strain sensors;
at least one receiver operatively coupled with said plurality of optical fiber strain sensors for reception of a returned portion of said electromagnetic radiation, said returned portion being returned by said plurality of optical fiber strain sensors;
at least one signal conditioner operatively coupled with said plurality of temperature sensors for measurement of temperatures proximate said plurality of optical fiber strain sensors;
a microprocessor operatively coupled with said receiver and said signal conditioner; and
a digital storage device operatively coupled with said microprocessor, said digital storage device containing instructions for execution by said microprocessor, said instructions including:
determining a plurality of apparent strains, one for each of said plurality of optical fiber sensors, said plurality of apparent strains being inferred from said returned portion of electromagnetic radiation;
determining a plurality of thermal bias components, one for each of said plurality of apparent strains, said plurality of thermal bias components being inferred from said temperatures proximate said plurality of optical fiber strain sensors; and
inferring an elastic strain for each of said plurality of optical fiber sensors based on said apparent strain and said thermal bias component of each of said plurality of optical fiber sensors.

17. The strain sensing system of claim 16, wherein each of said plurality of optical fiber sensors is a fiber Bragg grating.

18. The strain sensing system of claim 16 wherein said electromagnetic source is a laser.

19. The strains sensing system of claim 16 wherein each of said plurality of temperature sensors is a thermocouple.

20. A method for determining a force exerted on a distal end of a catheter, comprising:
providing a strain sensing assembly including a plurality of optical fiber strain sensors and a plurality of temperature sensors proximate said plurality of optical fiber strain sensors;
obtaining a plurality of temperature measurements, one each from said plurality of temperature sensors;
inferring a plurality of optical fiber strain sensor temperatures, one for each of said plurality of optical fiber strain sensors, said plurality of temperatures being inferred from said plurality of temperature measurements;
obtaining a plurality of apparent strain measurements, one for each of said plurality of optical fiber strain sensors;
inferring a plurality of thermal bias components, one for each of said plurality of optical fiber strain sensors, said plurality of thermal bias components being inferred from said plurality of optical fiber strain sensor temperatures;

inferring a plurality of elastic strains, one for each of said plurality of optical fiber strain sensors, from said plurality of apparent strain measurements and said plurality of thermal bias components; and determining a magnitude and a direction of said force exerted on said distal end of said catheter from said plurality of elastic strains.

21. The method of claim 20 wherein said step of inferring said plurality of thermal bias components is performed implicitly.

22. The method of claim 20 wherein said optical fiber strain sensors provided in the step of providing said strain sensing assembly comprises fiber-Bragg gratings.

23. The method of claim 20 wherein said plurality of optical fiber strain sensors provided in the step of providing said strain sensing assembly comprises three optical fiber strain sensors.

24. The method of claim 23 wherein said optical fiber strain sensors provided in the step of providing said strain sensing assembly comprises fiber-Bragg gratings.

25. A method for determining a force exerted on a distal end of a catheter, comprising:

providing a strain sensing assembly including a trio of optical fiber strain sensors and a plurality of temperature sensors proximate said trio of optical fiber strain sensors;

obtaining a plurality temperature measurements, one each from said plurality of temperature sensors;

inferring a trio of optical fiber strain sensor temperatures, one for each of said trio of optical fiber strain sensors, said plurality of temperatures being inferred from said plurality of temperature measurements;

obtaining a trio of apparent strain measurements, one for each of said trio of optical fiber strain sensors;

steps for determining a trio of elastic strains of said from said trio of optical fiber strain sensor temperatures and said trio of apparent strain measurements, one elastic strain for each of said trio of optical fiber strain sensors; and steps for determining a magnitude and a direction of said force exerted on said distal end of said catheter from said trio of elastic strains.

* * * * *